US009920147B2

(12) United States Patent
Zhang et al.

(10) Patent No.: US 9,920,147 B2
(45) Date of Patent: Mar. 20, 2018

(54) POLYMERIC MATERIALS HAVING ACTIVE CROSS-LINKERS, METHODS FOR MAKING THEM, AND USE THEREOF

(71) Applicant: BRANDEIS UNIVERSITY, Waltham, MA (US)

(72) Inventors: Ye Zhang, Waltham, MA (US); Bing Xu, Newton, MA (US)

(73) Assignee: Brandeis University, Waltham, MA (US)

( * ) Notice: Subject to any disclaimer, the term of this patent is extended or adjusted under 35 U.S.C. 154(b) by 0 days.

(21) Appl. No.: 15/021,394

(22) PCT Filed: Sep. 8, 2014

(86) PCT No.: PCT/US2014/054573
§ 371 (c)(1),
(2) Date: Mar. 11, 2016

(87) PCT Pub. No.: WO2015/076908
PCT Pub. Date: May 28, 2015

(65) Prior Publication Data
US 2016/0222148 A1 Aug. 4, 2016

Related U.S. Application Data

(60) Provisional application No. 61/877,772, filed on Sep. 13, 2013.

(51) Int. Cl.
*C08F 26/06* (2006.01)
*C08F 126/06* (2006.01)
(Continued)

(52) U.S. Cl.
CPC ........ *C08F 220/54* (2013.01); *C07F 15/0053* (2013.01); *C08F 226/02* (2013.01);
(Continued)

(58) Field of Classification Search
CPC ...... C08K 5/0025; C08K 5/0091; C08K 5/20; C08F 226/02; C08F 15/0053; C08F 220/54; C08L 33/26
(Continued)

(56) References Cited

U.S. PATENT DOCUMENTS 6,303,585 B1 10/2001 Spiro et al.
6,770,729 B2 8/2004 Van Antwerp
(Continued)

FOREIGN PATENT DOCUMENTS

WO 0194490 A1 12/2001
WO 2012061702 A1 6/2012

OTHER PUBLICATIONS

Zhang et al., "Structural Modulation of Self-Oscillating Gels: Changing the Proximity of the Catalyst to the Polymer Backbone to Tailor Chemomechanical Oscillation," Soft Matter 8:7056-7061 (May 31, 2012).*

(Continued)

*Primary Examiner* — William Cheung
(74) *Attorney, Agent, or Firm* — LeClairRyan, a Professional Corporation

(57) ABSTRACT

The present technology relates to a polymeric material including a plurality of polymer subunits and an active cross-linker, wherein the active cross-linker is covalently linked to the plurality of polymer subunits. The active cross-linker offers a key building block for constructing novel molecular architecture in chemomechanical soft materials and illustrates a new approach to tailor material properties.

12 Claims, 9 Drawing Sheets

(51) Int. Cl.
   *C08F 226/02*   (2006.01)
   *C08F 220/54*   (2006.01)
   *C08K 5/00*     (2006.01)
   *C08K 5/20*     (2006.01)
   *C07F 15/00*    (2006.01)
   *C08L 33/26*    (2006.01)

(52) U.S. Cl.
   CPC .......... *C08K 5/0025* (2013.01); *C08K 5/0091* (2013.01); *C08K 5/20* (2013.01); *C08L 33/26* (2013.01)

(58) Field of Classification Search
   USPC ...................................... 526/265, 259, 303.1
   See application file for complete search history.

(56)            References Cited

U.S. PATENT DOCUMENTS

| 6,989,197  | B2  | 1/2006  | Schneider        |
|------------|-----|---------|------------------|
| 7,241,009  | B2  | 7/2007  | Kornfield et al. |
| 8,414,911  | B2  | 4/2013  | Mattson et al.   |
| 2007/0259598 | A1 | 11/2007 | Ribi            |
| 2008/0095822 | A1* | 4/2008 | Maquet ................ A61K 9/0019 |
|            |     |         | 424/426          |
| 2008/0228268 | A1 | 9/2008 | Shannon et al.   |
| 2008/0236601 | A1 | 10/2008 | Jacobus         |
| 2010/0233112 | A1 | 9/2010 | Hu et al.        |
| 2012/0023677 | A9 | 2/2012 | Knight           |

OTHER PUBLICATIONS

Zhang et al., "Post-Self-Assembly Cross-Linking of Molecular Nanofibers for Oscillatory Hydrogels," Langmuir 28:3063-3066 (Jan. 25, 2012).*

International Search Report and Written Opinion for corresponding application No. PCT/US2014/054573, dated Sep. 30, 2015.

Zhang et al., "Post-Self-Assembly Cross-Linking of Molecular Nanofibers for Oscillatory Hydrogels," Langmuir 28:3063-3066 (2012), Jan. 25, 2012.

Zhang et al., "Structural Modulation of Self-Oscillating Gels: Changing the Proximity of the Catalyst to the Polymer Backbone to Tailor Chemomechanical Oscillation," Soft Matter 8:7056-7061 (2012), May 31, 2012.

Invitation to Pay Additional Fees PCT/ISA/206 Annex for corresponding application No. PCT/US2014/054573, dated Jul. 22, 2015.

Zhang et al., "Active Cross-Linkers That Lead to Active Gels," Angewandte Chemie International Edition 52 (44)11494-11498 (Sep. 12, 2013).

* cited by examiner

US 9,920,147 B2

POLYMERIC MATERIALS HAVING ACTIVE CROSS-LINKERS, METHODS FOR MAKING THEM, AND USE THEREOF

This application is a U.S. national stage application under 35 U.S.C. 371 of PCT international application PCT/US2014/054573, filed on Sep. 8, 2014 and claims the benefit of U.S. Provisional Patent Application Ser. No. 61/877,772, filed Sep. 13, 2013, the disclosure of which is incorporated herein by reference in its entirety.

This invention was made with government support under Army Research Office Grant ARO 56735-MS and NSF MRSEC Grant DMR-0820492. The government has certain rights in the invention.

FIELD OF THE INVENTION

This technology relates to the design and synthesis of active cross-linkers for creating a novel type of active soft material, in which the material properties are controlled by the active cross-linkers of the polymer network.

BACKGROUND OF THE INVENTION

Cross-linking, physically or covalently, is the fundamental and necessary attribute to introduce a 3D network in a polymer. Conventional bifunctional cross-linkers (e.g., bisacrylamide (Schild, *Prog. Polym. Sci.*, 17:163-249 (1992))) are inactive after the formation of the covalent crosslinks during the polymerization.

Whereas most cross-linkers in synthetic networks are less active, cross-linkers in biopolymer networks are active. For example, the cytoskeleton of muscle cells has myosin motors as the active cross-linkers to crosslink actin filaments (Rayment et al., *Science*, 261:58-65 (1993); Harada et al., *Nature* 326:805-808 (1987)). Marveled by this amazing machinery evolution of converting chemical energy to mechanical motion, researchers have spent considerable efforts on using actin and myosins to create active gels in vitro to explore the structures and dynamics of these minimal active networks (Kohler et al., *Nat. Mater.*, 10:462-468 (2011); Boal et al., *Small*, 2:793-803 (2006); Banerjee et al., *Soft Matter*, 7:463-473 (2011); Chen et al., *Soft Matter*, 7:355-358 (2011); Tsuchiya et al., *Angew. Chem.-Int. Edit.* 49:724-727 (2010)).

Although active or functional molecules are increasingly used for making supramolecular gels (Zhang et al., *Angew Chem.*, 124:7117-7121 (2012); Kohsaka et al., *Angew. Chem.-Int. Edit.*, 50:4872-4875 (2011); Tamesue et al., *Angew. Chem.-Int. Edit.*, 49:7461-7464 (2010); Kretschmann et al., *Angew. Chem.-Int. Edit.*, 45:4361-4365 (2006); Oku et al., *Angew. Chem.-Int. Edit.*, 43:966-969 (2004)) such as self-healing soft materials (Zhang et al., *Agnew Chem.*, 124:7117-7121 (2012); Imato et al., *Angew. Chem.-Int. Edit.*, 51:1138-1142 (2012); Amamoto et al., *Angew. Chem.-Int. Edit.*, 50:1660-1663(2011); Wang et al., *Nature*, 463:339-343 (2010)), synthetic polymeric gels with active cross-linkers have not been generated.

$[Ru(bipy)_3]^{n+}$ is as a well-known coordination compound (Balzani et al., *Chem. Rev.*, 96:759-833 (1996); Crosby et al., *J. Chem. Phys.*, 43:1498 (1965); Caspar et al., *J. Am. Chem. Soc.*, 105:5583-5590 (1983); Maness et al., *J. Am. Chem. Soc.*, 118:10609-10616 (1996)) and has long lifetime of excited state that has both oxidizing and reducing properties. Its derivatives have served as photosensitizers (Demas et al., *J. Am. Chem. Soc.*, 93:1800 et seq. (1971); Meyer, *Accounts Chem. Res.*, 22:163-170 (1989); Kalyanasundaram et al., *Coord. Chem. Rev.*, 177:347-414 (1998)), electrochemiluminescent components (Tokel et al., *J. Am. Chem. Soc.*, 94:2862 et seq. (1972)), the core of a bacteria sensing element (Grunstein et al., *J. Am. Chem. Soc.*, 133:13957-13966 (2011)), a component for conducting polymers (Zhu et al., *J. Mater. Chem.*, 9:2123-2131 (1999)), and the cores of star polymers (Lamba et al., *J. Am. Chem. Soc.*, 119: 1801-1802 (1997); Collins et al., *Macromolecules*, 31:6715-6717 (1998); McAlvin et al., *Macromolecules*, 32:6925-6932 (1999)).

$[Ru(bipy)_3]^{n+}$ also serves as a redox catalyst for a well-established chemical oscillator, namely the Belousov-Zhabotinsky (BZ) reaction (Bansagi et al., *Science*, 331: 1309-1312 (2011); Noszticzius et al., *J. Am. Chem. Soc.*, 101:3177-3182 (1979); Maselko et al., *J. Chem. Phys.*, 85:6430-6441 (1986); Vanag et al., *Phys. Rev. Lett.*, 86:552-555 (2001); Vanag et al., *Phys. Rev. Lett.*, 87:228301 (2001); Zeyer et al., *J. Phys. Chem. A*, 102:9702-9709 (1998); Bolletta et al., *J. Am. Chem. Soc.*, 104:4250-4251 (1982)). The redox switch of $[Ru(bipy)_3]^{n+}$ complex has led to the development of a self-oscillating gel that swells in oxidized state (Ru(III)) and shrinks in reduced state (Ru(II)) during the BZ reaction (Yoshida et al., *J. Am. Chem. Soc.*, 118: 5134-5135 (1996)). However, in that type of gel, N,N'-methylenebisacrylamide (BIS) (Yoshida, *Adv. Mater.*, 22:3463-3483 (2010)) is the cross-linker and the ruthenium (II/III) complex is a pendant of the cross-linked chains of poly(NIPAAm) (Schild, *Prog. Polym. Sci.*, 17:163-249 (1992); Chen et al., *Nature*, 373:49-52 (1995); Eliassaf, *J. Appl. Polym. Sci.*, 22:873-874 (1978); Park et al., *Biotechno. Prog.*, 10:82-86 (1994).

Active polymers have broad technological applications. However, there are limited methods to produce such materials except memory alloys and temperature responsive gels, where the polymer subunits of the gels are responsive to temperature. The present invention overcomes these and other deficiencies in the art.

SUMMARY OF THE INVENTION

This technology relates to a polymeric material comprising a plurality of polymer subunits and an active cross-linker, wherein the active cross-linker is covalently linked to the plurality of polymer subunits.

This technology also relates to a method of producing a polymeric material. The method includes polymerizing a plurality of polymer subunits with an active cross-linking agent, wherein the active cross-linking agent is covalently linked to the plurality of polymer subunits.

This technology further relates to a chemomechanical material including a polymeric material comprising a plurality of polymer subunits and an active cross-linker, wherein the active cross-linker is covalently linked to the plurality of polymer subunits to form a stimuli responsive shape changing polymeric network.

This technology also relates to a compound of the formula:

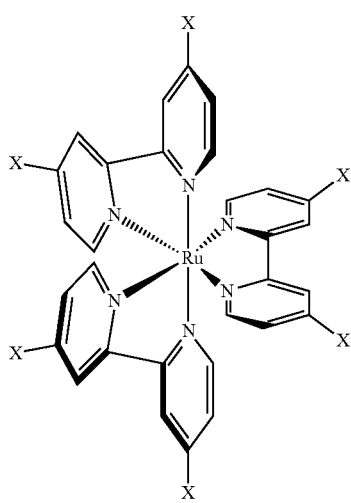

wherein each X is optionally present and has the formula

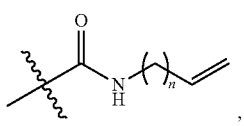

wherein n is an integer from 1 to about 20 and with the proviso that at least one X is present.

This technology further relates to a compound of the formulae:

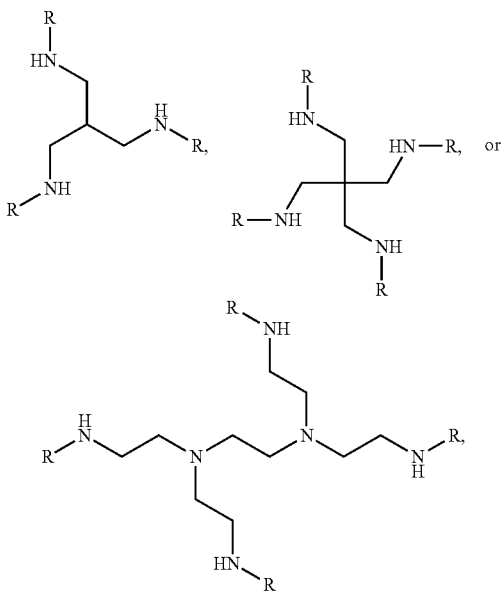

wherein R is

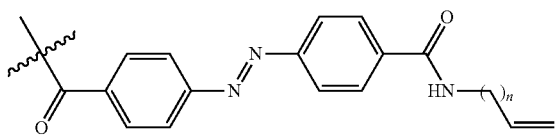

and n is an integer from 1 to about 20.

The present technology relates to the design and synthesis of active cross-linkers for creating a novel type of active soft material useful as a chemomechanical material. This technology also relates to a new way to control molecular architecture for active materials in which the active cross-linkers of the polymer network command the material properties. In accordance with this technology, shape changing soft materials can be produced for use in chemomechanical applications, such as biomedical products, cosmetic products, and actuators. The method of the present technology provides a simple, powerful, and general way to construct active soft materials as compared to existing technology using various polymer backbones and resulting in different chemomechanical behaviors compared to existing chemomechanical materials.

Moreover, the present technology enables the transformation of a thermally insensitive polymer (e.g., poly(allylamine)) into a self-oscillatory material by the use of active cross-linkers, illustrating that polymerization with active cross-linkers is an effective approach to generate active soft materials.

BRIEF DESCRIPTION OF THE DRAWINGS

FIG. 8A shows a confocal fluorescent image of Gel$_1$. FIG. 8B shows a confocal fluorescent image of Gel$_2$. FIG. 8C shows a 3D image of Gel$_1$. FIG. 8D shows a 3D image of Gel$_2$.

FIG. 9A shows a confocal fluorescent image of Gel$_3$. FIG. 9B shows a confocal fluorescent image of Gel$_4$. FIG. 9C shows a 3D image of Gel$_3$. FIG. 9D shows a 3D image of Gel$_4$.

FIGS. 11A-D show the relative diameters (which reflect equilibrium swelling ratio) of Gel$_1$ (FIG. 11A), Gel$_2$ (FIG. 11B), comparison Gel$_3$ (FIG. 11C) (Yoshida et al., *J. Am. Chem. Soc.*, 118:5134-5135 (1996), which is hereby incorporated by reference in its entirety), and comparison Gel$_4$ (FIG. 11D) in a reduced state (Ru(II)) and an oxidized state (Ru(III)), as a function of temperature. FIGS. 11E-F show the mechanical oscillation profile of Gel$_1$ (FIG. 11E) and Gel$_2$ (FIG. 11F) during the BZ reaction. (Reaction conditions: [malonic acid]=0.4 M, [BrO$_3^-$]=0.2 M, [HNO$_3$]=0.4 M, temperatures for Gel$_1$ and Gel$_2$ were 10° C. and 15° C., respectively).

DETAILED DESCRIPTION OF THE INVENTION

Figure 1:
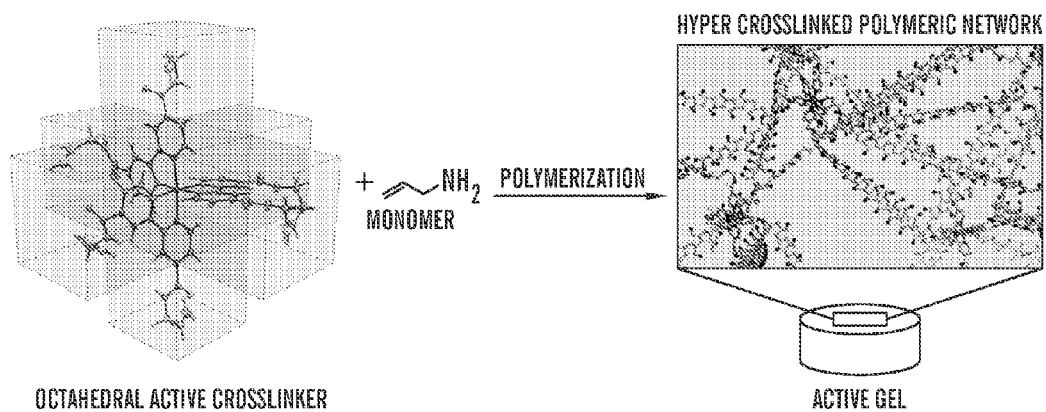
FIG. 1 is a schematic illustrating the formation of an active polymeric gel in accordance with one embodiment of the present technology including an active cross-linker and allylamine polymer subunits.

This technology relates to a polymeric material comprising a plurality of polymer subunits and an active cross-linker, wherein the active cross-linker is covalently linked to the plurality of polymer subunits.

As used herein, the term "polymer" or "polymeric" is used broadly and includes, for example, homopolymers, copolymers, graft polymers, dendrimer polymers, block copolymers, interpenetrating networks, semi-interpenetrating networks, and polymer blends. These terms are used interchangeably herein to refer generally to the combined the products of a single chemical polymerization reaction. Polymers are produced by combining monomer or oligomer subunits into a covalently bonded chain or network. Polymers that contain only a single type of monomer are known as "homopolymers", while polymers containing a mixture of monomers are known as "copolymers."

The term "polymerizable moiety" referrers to a functional group that is capable of participating in a polymerization reaction and, through the polymerization reaction, can be converted into a component of a polymer. Representative "polymerizable moieties" include, but are not limited to, vinyl, acryloyl, carboxylic acids, esters, anhydrides, aldehydes, ureas, etc. Additional "polymerizable moieties" are known to those of skill in the art and are described, for example, in Seymor et al., Polymer Chemistry 2$^{nd}$ edition, Marcel Dekker, Inc., New York (1988), which is hereby incorporated by reference in its entirety.

The term "monomer" refers to a molecule that can undergo polymerization or copolymerization thereby contributing constitutional units to the essential structure of a macromolecule (a polymer).

As used herein, "oligomer" or "oligomeric" refers to a polymer having a finite and moderate number of repeating monomer structural units. Oligomers of the invention typically have 2 to about 100 repeating monomer units; frequently 2 to about 30 repeating monomer units; and often 2 to about 10 repeating monomer units; and usually have a molecular weight up to about 3,000.

The skilled artisan will appreciate that oligomers and polymers may, depending on availability of polymerizable groups or side chains, subsequently be incorporated as monomers in further polymerization or cross-linking reactions.

The term "gel" refers to a three-dimensional polymeric structure that itself is insoluble in a particular liquid but which is capable of absorbing and retaining large quantities of the liquid to form a stable, often soft and pliable, structure. When the liquid is water, the gel is referred to as a hydrogel.

"Cross-linking", as used herein, refers to the attachment of two or more monomers, oligomers or longer polymer chains by bridges of a cross-linker, such as an element, molecular group, a compound, or another oligomer or polymer. Cross-linking can result in a polymeric network (which can be two-dimensional or three-dimensional) where the polymer subunits are interconnected with multiple cross-linking agents and without free ends. Cross-linking may take place upon exposure to a stimulus, such as heat or light. As a result, some cross-linking processes occur at increased temperature, and some may also occur at room temperature or at lower temperature. As cross-linking density is increased, the properties of a material can be changed from thermoplastic to thermosetting.

As used herein, the term "active cross-linker" or "active cross-linking agent" refers to a chemical entity which attaches two or more monomers, oligomers, or longer polymer chains (i.e., polymer subunits) in a polymeric chain or network (which can be two-dimensional or three-dimensional) and which is responsive to a stimulus after the formation of covalent cross-links during polymerization. The active cross-linker is a separate component including two or more polymerizable moieties which can react with functional groups in the polymer subunits to form linkages (or bridges) between two or more different polymer subunits.

In accordance with one embodiment of the present technology, the polymeric material is a "soft material" selected from the group consisting of a gel, an elastomer, a rubber, a film, a foam, an aerogel, and a sponge.

In accordance with another embodiment of the present technology, the polymeric material is a shape changing material, such as a shape changing polymeric gel.

The polymer subunits in the polymeric material may be selected from the group consisting of monomers, oligomers, and combinations thereof. In one embodiment, the active cross-linker covalently linked to the plurality of polymer subunits forms a three-dimensional polymeric network. In another embodiment, the polymer subunits are synthetic polymer subunits.

Suitable monomers for the polymer subunits include, but are not limited to, N-isopropylacrylamide, allylamine, functionalized acrylic, methacrylic, and combinations thereof. Other examples include, but are not limited to, NBR, HNBR, XNBR, EPDM, thermo plastic elastomers (TPE), and combinations thereof, which are useful when using vulcanization. Other suitable monomers are known in the art and are determined by the desired properties and characteristics of the resulting polymeric material.

In accordance with one embodiment of the present technology, the active cross-linker is a stimuli-responsive (sensitive) cross-linker. Suitable stimuli-responsive cross-linkers include, but are not limited to, redox-responsive cross-linkers, light-responsive cross-linkers, brine-responsive cross-linkers, pH-responsive cross-linkers, gas-responsive cross-linkers, and temperature-responsive cross-linkers.

In one embodiment, the active cross-linker is a redox-responsive cross-linker. As used herein, a redox-responsive cross-linker is a cross-linker that remains active after the formation of the covalent cross-links during polymerization and is responsive to oxidizing and/or reducing agents. In one embodiment, the polymeric material of the present technology including a redox-responsive active cross-linker changes shape or volume due to the chemical reduction and oxidation of the redox-responsive active cross-linker.

In a further embodiment, the active cross-linker is a ruthenium bipyridine complex. In accordance with a certain embodiment, the ruthenium bipyridine complex may have the structure $[RuL_3]^{n+}$, wherein L is selected from the group consisting of N,N'-diallyl-[2,2'-bipyridine]-4,4'-dicarboxamide, N-allyl-[2,2'-bipyridine]-4-carboxamide, 2,2'-bipyridine, 4-methyl-4'-vinyl-2,2'-bipyridine, and combinations thereof, and n is 2 or 3.

In one embodiment, the ruthenium bipyridine complex has the formula:

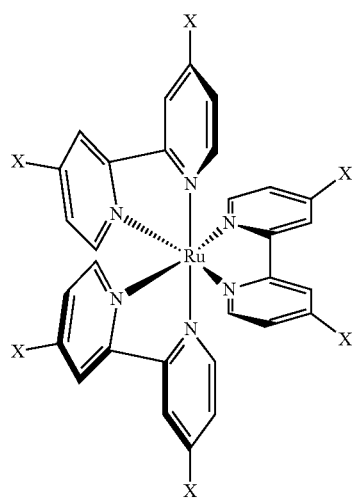

wherein each X is optionally present and has the formula

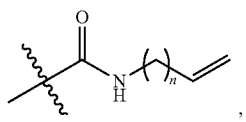

wherein n is an integer from 1 to about 20 and with the proviso that at least one X is present.

In certain embodiments, the complex has the formula:

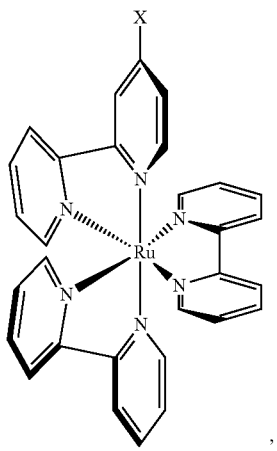

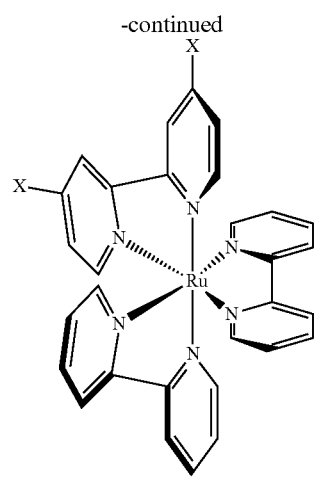

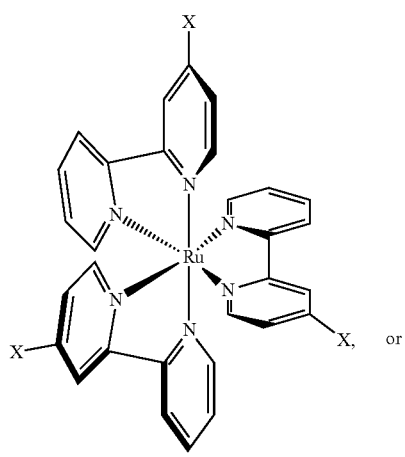

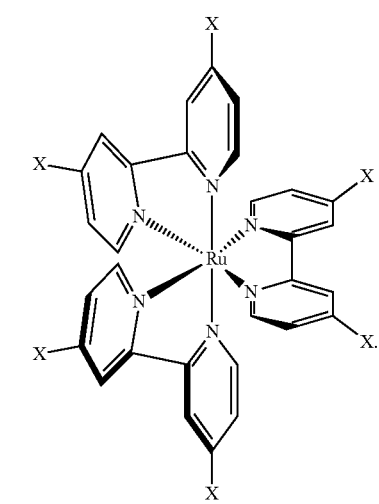

Suitable examples of ruthenium bipyridine complexes in accordance with the present technology include, but are not limited to,

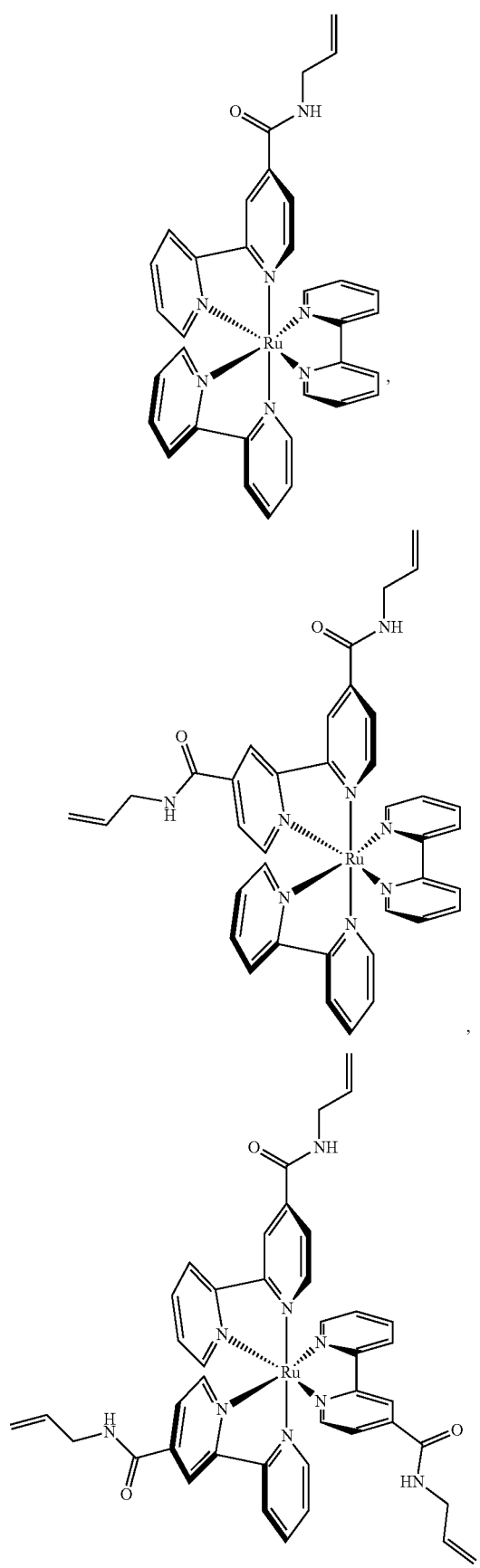,

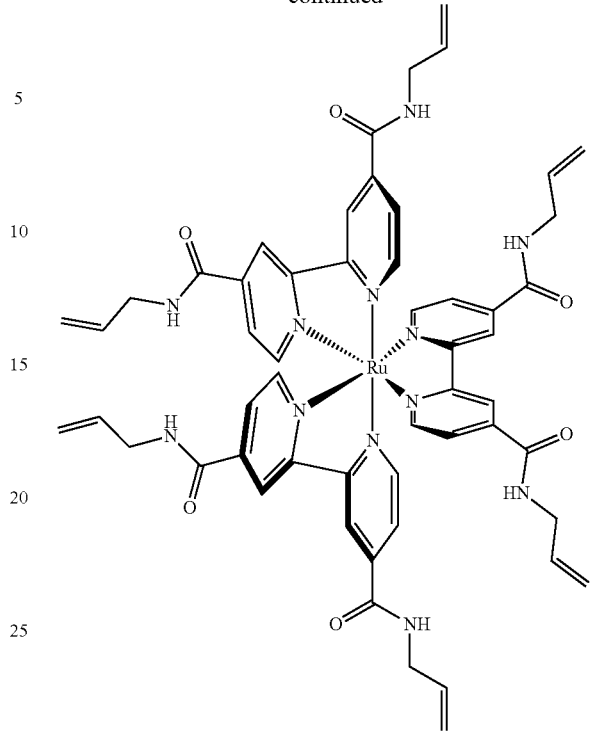

In one particular embodiment, this technology relates to the design and synthesis of the first octahedral ruthenium bipyridine complex that bears six polymerizable vinyl groups serving as the active cross-linker for creating a novel type of active soft material. In accordance with this embodiment, the ruthenium bipyridine complex has the structure below:

Formula I

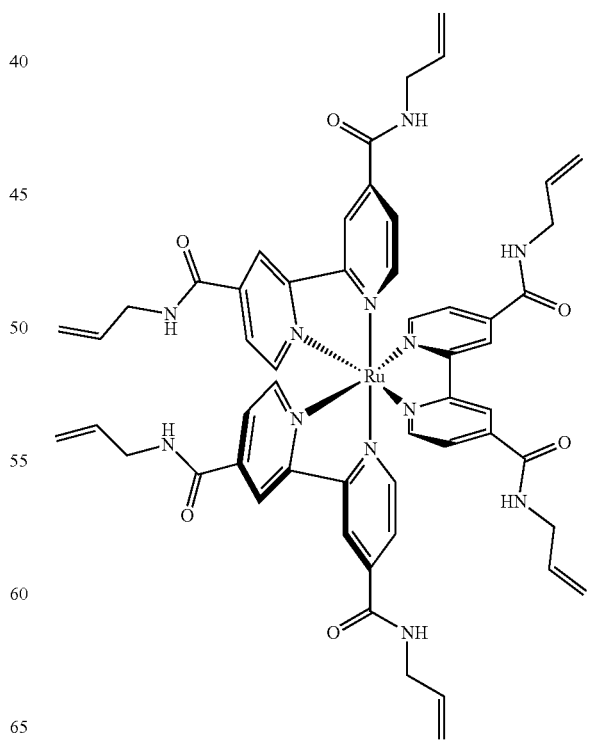

Figure 2:
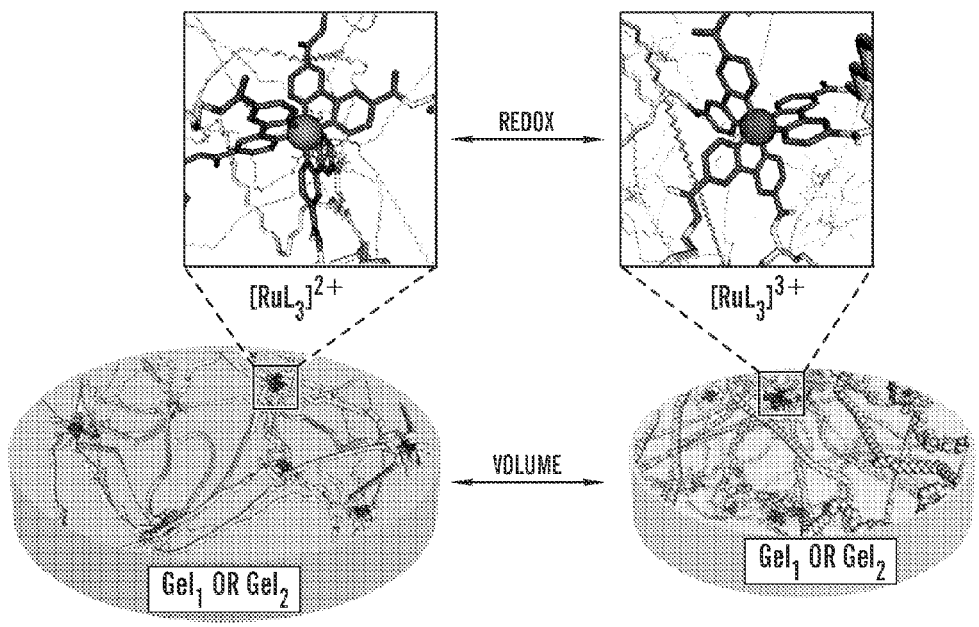
FIG. 2 is a schematic illustrating active polymeric gels in accordance with certain embodiments of the present technology and the volumetric oscillation of the gels induced by the redox switch of the active cross-linker during the BZ reaction (side chains of the polymers are omitted for clarity).

A polymeric material in accordance with the present technology including a ruthenium bipyridine complex as the active cross-linker is illustrated in FIGS. 1 and 2. As shown in the embodiment of FIGS. 1 and 2, the polymeric material is an active gel which exhibits volumetric oscillation induced by the redox switch of the active cross-linker of Formula I during the BZ reaction. Although FIGS. 1 and 2 show the active cross-linker of Formula I, other active cross-linkers in accordance with the present technology could be used. The capacity of a $[Ru(bipy)_3]^{n+}$ derivative as an active cross-linker has never previously been investigated. Because of the stereochemical configuration of the $[RuL_3]^{n+}$ complex, its application as a cross-linker results in an unprecedented molecular architecture for developing active soft materials as chemomechanical materials.

In yet another embodiment, the active cross-linker is a light-responsive cross-linker. As used herein, a light-responsive cross-linker is a cross-linker that remains active after the formation of the covalent cross-links during polymerization and is responsive to light.

Suitable examples of light-responsive active cross-linkers include, but are not limited to,

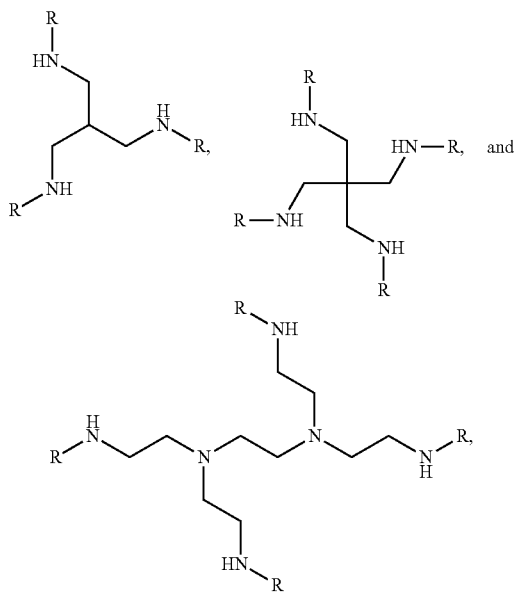

wherein R is

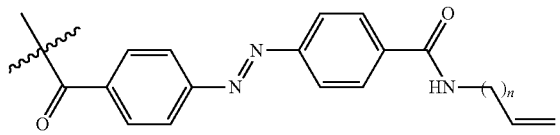

and n is an integer from 1 to about 20.

Suitable brine-responsive cross-linkers are cross-linkers which are ionic and have an acid or base group. The water diffusion in and out of the polymer is affected by the ion strength and the type of ion (+ or 2+, for example) of the brine. Suitable pH-responsive cross-linkers include cross-linkers of the amine type, where a change of pH will change the charge of the cross-linker thus changing the amount of water the polymer can hold. Suitable gas-responsive cross-linkers include, for example, primary amine containing cross-linkers that react with $CO_2$. Suitable temperature-responsive cross-linkers include, for example, cross-linkers containing isopropylacrylamide.

In accordance with one embodiment of the present technology, the active cross-linker includes from about 1 to about 30 polymerizable moieties. In one embodiment, the active cross-linker includes from 1 to about 6 polymerizable moieties. Suitable polymerizable moieties are known in the art and include, for example, vinyl, acryloyl, carboxylic acids, esters, anhydrides, aldehydes, and ureas. Additional "polymerizable moieties" are known to those of skill in the art and are described, for example, in Seymor et al., Polymer Chemistry $2^{nd}$ edition, Marcel Dekker, Inc., New York (1988), which is hereby incorporated by reference in its entirety. In one particular embodiment, the polymerizable moiety is a vinyl moiety. In accordance with the present technology, the active cross-linker is directly linked to the polymer subunits through the polymerizable moieties present in the active cross-linker.

By controlling the initial ratio of the polymer subunit (e.g., monomer) versus the active cross-linker, polymer materials with a desired elasticity can be produced. In one embodiment, the molar ratio of the polymer subunit to the active cross-linker is from about 1:1 to about $1 \times 10^8$: 1. In one particular embodiment, the molar ratio of the polymer subunit to the active cross-linker is about 1:0.004.

The present technology also relates to a method for producing a polymeric material. The method includes polymerizing a plurality of polymer subunits with an active cross-linking agent, wherein the active cross-linking agent is covalently linked to the plurality of polymer subunits.

The active cross-linking agent may be prepared by methods known to those skilled in the art. One method for preparing an active cross-linker of the present technology includes the following two-step synthesis. First, 4,4'-dicarboxyl-2,2'-bipyridine (Sprintschnik et al., J. Am. Chem. Soc. 98:2337-2338 (1976); Giordano et al., J. Am. Chem. Soc. 99:3187-3189 (1977), which are hereby incorporated by reference in their entirety) reacts with two equivalents of allylamine in the presence of coupling reagents to form N,N'-diallyl-[2,2'-bipyridine]-4,4'-dicarboxamide. Second, six equivalents of N,N'-diallyl-[2,2'-bipyridine]-4,4'-dicarboxamide react with one equivalent of dichloro(p-cymene)ruthenium(II) dimer (Zhou et al., Inorg. Chem. 44:8317-8325 (2005), which is hereby incorporated by reference in its entirety) in DMF at 120° C. under $N_2$ for 12 hours. After the reaction completes, purification is performed through column chromatography (Zhang et al., Soft Matter 8:3056-3061 (2012); Zhang et al., Langmuir 28:3063-3066 (2012), which are hereby incorporated by reference in their entirety), and the removal of solvent affords the active cross-linker of Formula I. This method is described in further detail in the Examples below.

Suitable techniques for polymerizing are known in the art and include, for example, free radical polymerization, ionic polymerization, condensation polymerization, coordination polymerization, and atom transfer radical polymerization. In one embodiment, polymerizing is carried out using a photopolymerization process.

In a typical photopolymerization method, the monomer and cross-linker are irradiated with ultraviolet (UV) rays in the presence of a photopolymerization initiator (i.e., photoinitiators). Suitable photoinitiators are those available under the trade designations IRGACURE and DAROCUR from Ciba Specialty Chemical Corp., Tarrytown, N.Y. and include, for example, 1-[4-(2-hydroxyethoxy)phenyl]-2-hydroxy-2methyl-1-propane-1-one (IRGACURE 2959), 1-hydroxycyclohexyl phenyl ketone (IRGACURE 184), 2,2-dimethoxy-1,2-diphenylethan-1-one (IRGACURE 651), bis-(2,4,6-trimethylbenZoyl)phenylphosphineoxide (IRGACURE 819), 2-benzyl-2-dimethylamino-1-(4-morpholinophenyl)butanone(IRGACURE 369), 2-methyl-1-[4-(methylthio)phenyl]-2-morpholinopropan-1-one (IRGACURE 907), and 2-hydroxy-2-methyl-1-phenyl propan-1-one (DAROCUR 1 173). In one embodiment, the photoinitiators are selected from the group consisting of IRGACURE 2959, 819, and 184.

Other suitable initiators are well known in the art and include, for example, 1,1-diphenylhexyllithium, n-butyllithium, phenyl magnesium-chloride, and the anionic living oligomer of styrene or α-methyl styrene.

Initiators can be employed in concentrations ranging from about 0.0001 to about 3.0 pbW, or from about 0.001 to about 1.0 pbW, or from about 0.005 to about 0.5 pbW, per 100 pbW of the monomer composition.

Other additives which are known to those of ordinary skill in the art may be present in the polymerization mixture. For example, LiCl is often used as an additive in the anionic polymerization of the acrylic monomers (Fayt et al., Macromolecules 20:1442 et seq. (1987), which is hereby incorporated by reference). In addition, an activator may be present in the polymerization mixture. Suitable activators for cationic polymerization include weak acids, such as Lewis acids. Such Lewis acids include, but are not limited to, $AlCl_3$, $EtAlCl_2$, $Et_2AlCl$, $Et_3Al$, $ZnCl_2$, $ZnBr_2$, $ZnI_2$, $SnCl_2$, $SnCl_4$, $SnBr_4$, and $I_2$.

Mixing of the monomer, active cross-linker, and initiator can be carried out by conventional mixing techniques, such as stirring, rocking, kneading, and the like. In some cases, especially when the monomer and/or active cross-linker are not liquids, the mixing can be effected by dissolving either or both in a suitable solvent. Suitable solvents include, but are not limited to, methanol, THF, 1,4-dioxane, 1,3-dioxane, benzene, toluene, xylene, hexane, heptane, octane, cyclohexane, dichoromethane, chloroform, and carbon tetrachloride.

Yet another embodiment of the present technology relates to a chemomechanical material. The chemomechanical material includes a polymeric material comprising a plurality of polymer subunits and an active cross-linker, wherein the active cross-linker is covalently linked to the plurality of polymer subunits to form a stimuli responsive shape changing polymeric network.

In one embodiment, the chemomechanical material is selected from the group consisting of a biomedical product (e.g., medium for tissue engineering), a cosmetic product (e.g., hair gel), and an actuator.

In accordance with one embodiment of the present technology, the stimulus is a redox agent. Suitable redox agents are determined by the active cross-linker used and can be, for example, cerium sulfate and cerium nitrate.

In accordance with another embodiment of the present technology, the stimulus is light.

In accordance with a further embodiment of the present technology, the stimulus is fluids with different ion strengths and types of ions.

Other suitable stimuli are described above with regard to stimuli responsive active cross-linkers.

In another embodiment, this technology relates to a compound of the formula:

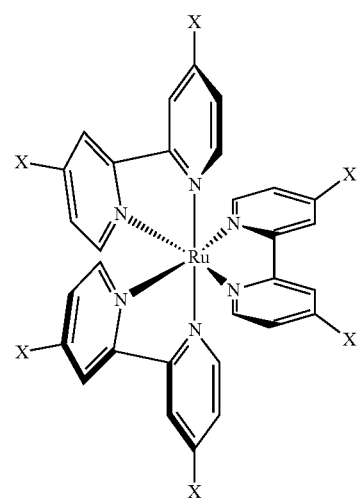

wherein each X is optionally present and has the formula

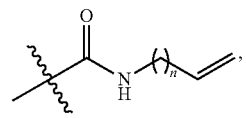

wherein n is an integer from 1 to about 20 and with the proviso that at least one X is present.

In accordance with certain embodiments of the present technology, X can be present in one, two, three, or six positions.

In one particular embodiment, the compound has the formula:

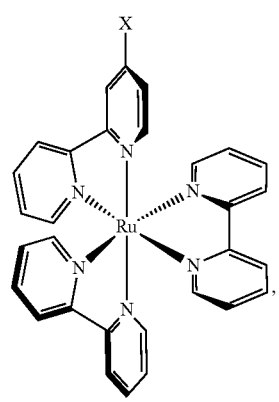

-continued
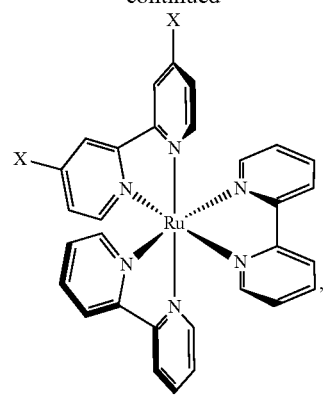
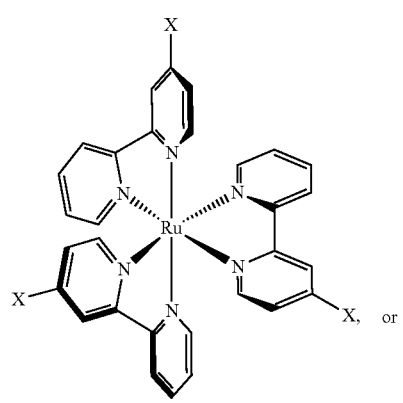, or
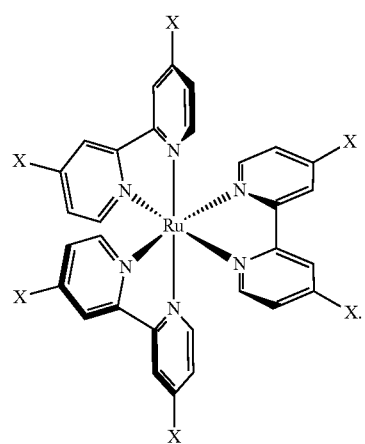
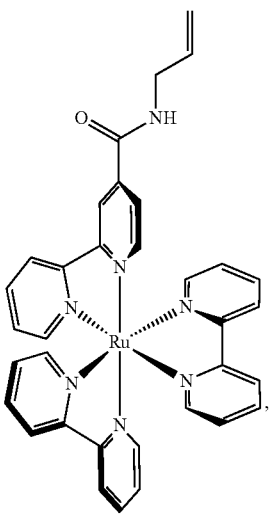
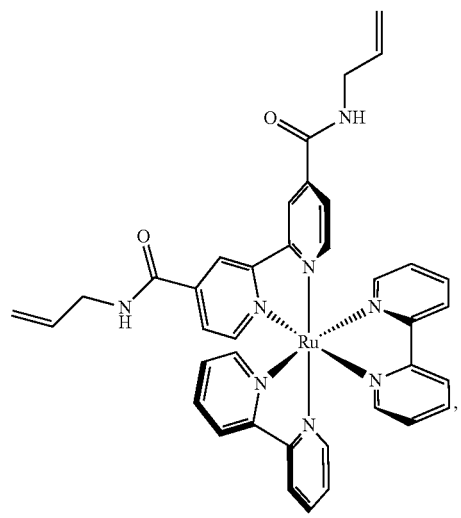
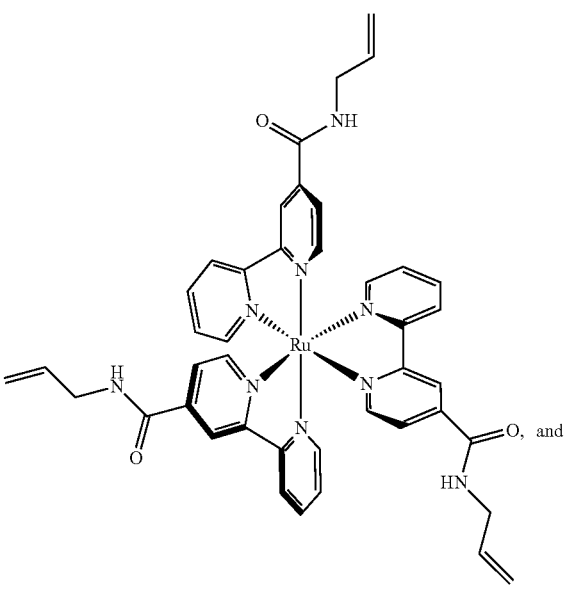, and
In a further embodiment, the compound is selected from the group consisting of:

In one embodiment, the compound has the formula:

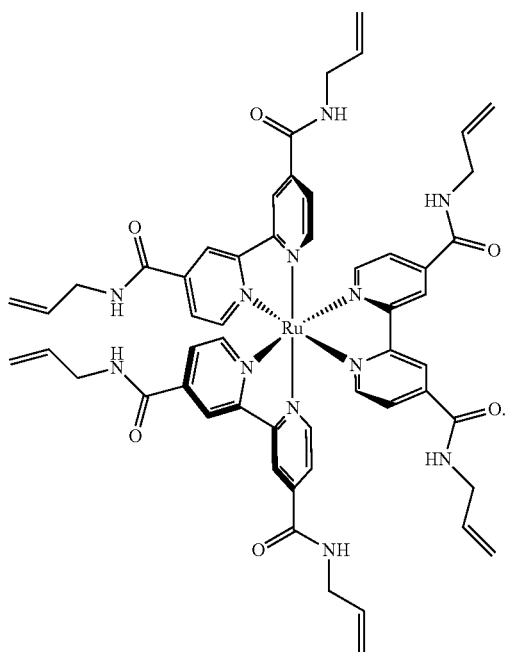

In another embodiment, this technology further relates to a compound of the formulae:

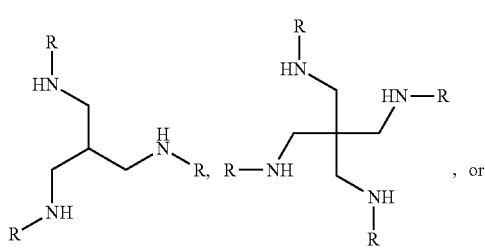

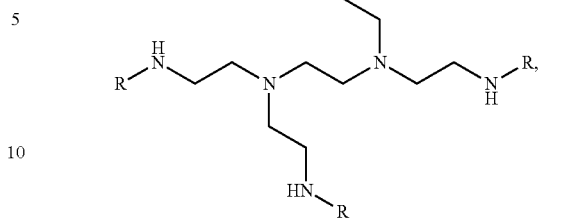

wherein R is

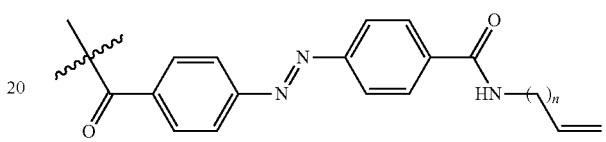

and n is an integer from 1 to about 20.

In accordance with the present technology, the chemomechanical material changes shape in response to a stimulus for the active cross-linker. In one particular embodiment, the chemomechanical material is a self-oscillatory material including a redox-responsive active cross-linker in accordance with the present technology.

By designing and synthesizing active cross-linkers for polymeric materials, including the first octahedral ruthenium bipyridine complex that bears six polymerizable vinyl groups as the active cross-linker, a new way to control molecular architecture for active materials in which the active cross-linkers of the polymer network command the material properties has been developed. In particular, a new way for making active soft materials using an active catalyst as the cross-linker of polymer network has been developed. Moreover, this technology multiplies the diversity of available active materials, which lays the molecular foundation for combining the counter-acting components to construct sophisticated chemomechanical systems or materials (Thompson et al., *Science*, 292:2469-2472 (2001), which is hereby incorporated by reference in its entirety). Furthermore, this technology also offers a key building block for the construction of new redox active polymers from the octahedral ruthenium complex.

EXAMPLES

The following examples are provided to illustrate embodiments of the present invention but are by no means intended to limit its scope.

Example 1—Materials and Methods

Anhydrous DMF, 4,4'-dimethyl-2,2'-bipyridine (99.5%), N,N-diisopropylethylamine (DIEA), allylamine (98%), and dichloro(p-cymene)ruthenium(II) dimmer, 2-hydroxy-4'-(2-hydroxyethoxy)-2-methylpropiophenone (Irgacure 2959), N-isopropylacrylamide (NIPAAm) (≥99%) were purchased from Sigma-Aldrich. O-benzotriazole-N,N,N',N'-tetramethyl-uronium-hexafluoro-phosphate (HBTU) was purchased from GL Biochem. Sephadex LH-20 was purchased from GE Healthcare.

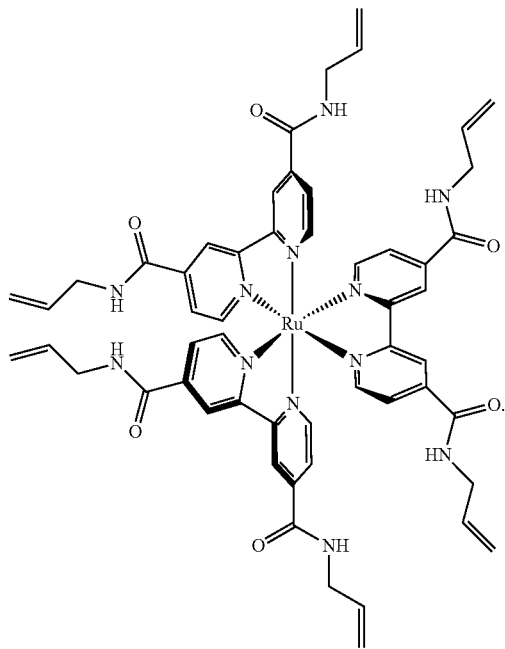

Example 2—Synthesis of N,N'-diallyl-[2,2'-bipyridine]-4,4'-dicarboxamide

Figure 3A:
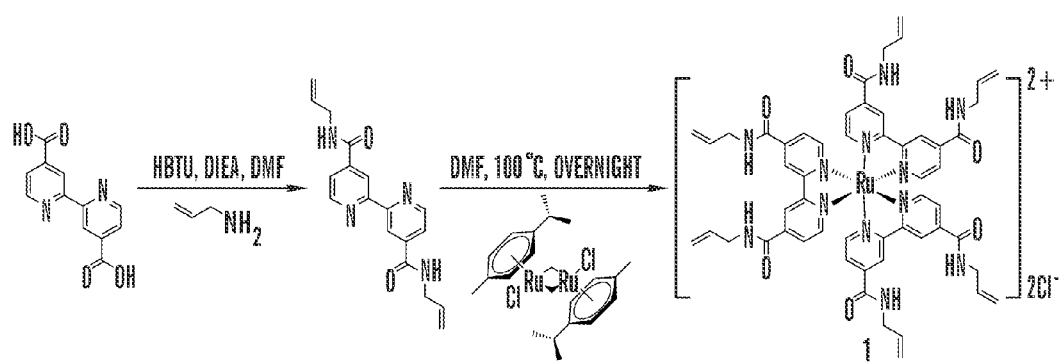
FIG. 3A shows the synthesis of an active cross-linker in accordance with one embodiment of the present technology. DIEA=diisopropylehtylamine, DMF=N,N-dimethylformamide, HBTU=O-(benzo-triazol-1-yl)-N,N,N',N'-tetramethyluronium hexafluorophosphate.
Figure 4:
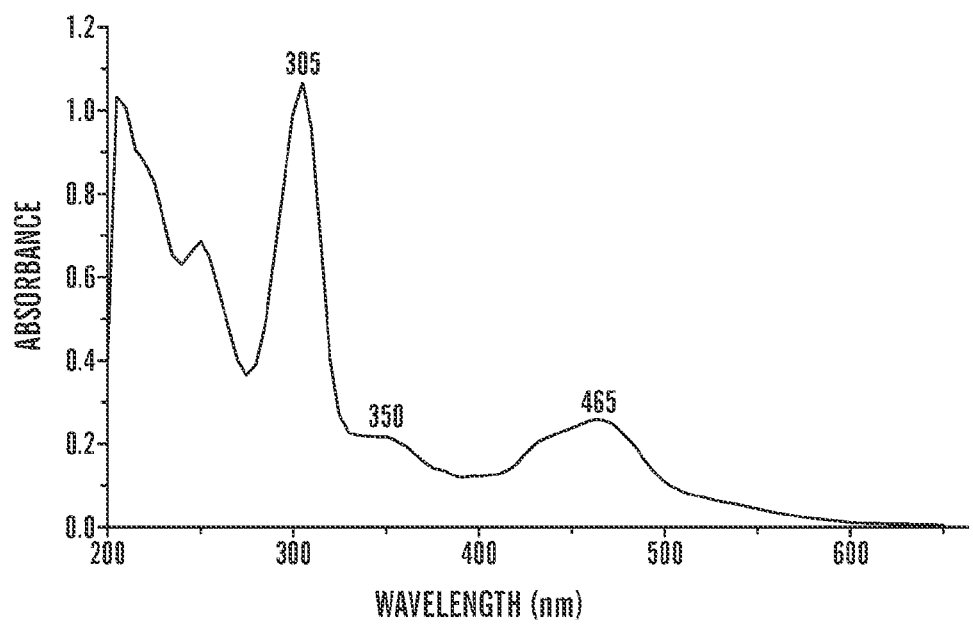
FIG. 4 shows UV-vis absorbance of an active cross-linker in accordance with one embodiment of the present technology at a concentration of 25.5 μmol/L in water.

As shown in FIG. 3A, 4,4'-dicarboxy-2,2'-bipyridine (5 mmol, 1.22 g) and HBTU (15 mmol, 5.7 g) were charged in a round bottom flask, and anhydrous DMF (15 mL) was added into the flask. The mixture was stirred at room temperature until mixed well. DIEA (30 mmol, 3.8 mL) was added into the mixture and kept stirring for 10 minutes. Then allylamine (25 mmol, 1.87 mL) was slowly added into the flask. After overnight stirring, the precipitates were collected and washed by ethyl acetate to obtain white crystals as the pure product in a yield of 85%. $^1$H NMR (400 MHz, DMSO-$d_6$) δ 9.16 (s, 2H), 8.87 (d, J=4.4 Hz, 2H), 8.82 (s, 2H), 7.87 (d, J=4.4 Hz, 2H), 5.97-5.87 (m, 2H), 5.21 (d, J=17.2 Hz, 2H), 5.12 (d, J=10.4 Hz, 2H), 3.96 (s, 4H) ppm.

Example 3—Synthesis of Active Cross-Linker of Formula I

As further shown in FIG. 3A, N,N'-diallyl-[2,2'-bipyridine]-4,4'-dicarboxamide from Example 2 (3 mmol, 967 mg) and dichloro(p-cymene)ruthenium(II) dimer (0.5 mmol, 306 mg) were charged into a two-neck round bottom flask that connected to a condenser.Anhydrous DMF (10 mL) was added into the flask and the solution was purged with $N_2$ for 30 minutes. Then the solution was refluxed under $N_2$ and dark conditions for 12 hours. After removing the solvent, the crude product was purified through a Sephadex column by using methanol as the eluent. The active cross-linker of Formula I was obtained as dark red powder in a yield of 61%. $^1$H NMR (400 MHz, DMSO-$d_6$) δ 9.69 (d, J=5.2 Hz, 6H), 9.35 (s, 6H), 9.00 (s, 6H), 8.11 (d, J=5.2 Hz, 6H), 5.97-5.90 (m, 6H), 5.26 (d, J=16.8 Hz, 6H), 5.17 (d, J=9.6 Hz, 6H), 4.02 (s, 12H) ppm.

Example 4—UV-Vis Spectrum of Active Cross-Linker of Formula I

The UV-vis spectrum was recorded on Varian 50 Bio UV-visible spectrophotometer.

FIG. 4 shows the UV-vis absorbance spectrum of the active cross-linker of Formula I and exhibits four absorption bands at 200, 250, 305 and 465 nm. The 200 and 305 nm bands arise from the ligand-centered (LC) π-π* transitions (Poizat et al., *J. Phys. Chem.*, 95:1245-1253 (1991), which is hereby incorporated by reference in its entirety), the remaining intense bands at 250 and 465 nm belong to metal-to-ligand charge transfer (MLCT) d-π* transitions, and the shoulder at 350 nm reflects metal-centered (MC) transitions (Juris et al., *Coord. Chem. Rev.*, 84:85-277 (1988), which is hereby incorporated by reference in its entirety). These peaks indicated that the active cross-linker of Formula I electronically resembles the [Ru(bipy)$_3$]Cl$_2$ complex, thus it should be able to function as a desired redox catalyst of the BZ reaction (Zeyer et al., *J. Phys. Chem. A*, 102:9702-9709 (1998); Bolletta et al., *J. Am. Chem. Soc.*, 104:4250-4251 (1982), which are hereby incorporated by reference in their entirety).

Example 5—Single Crystal Structure of Active Cross-Linker of Formula I

All operations were performed on a Bruker-Nonius Kappa Apex2 diffractometer, using graphite-monochromatedMoKα radiation. All diffractometer manipulations, including data collection, integration, scaling, and absorption corrections were carried out using the Bruker Apex2 software (Apex2, Version 2 User Manual, M86-E01078, Bruker Analytical X-ray Systems, Madison, Wis., June 2006, which is hereby incorporated by reference in its entirety). Preliminary cell constants were obtained from three sets of 12 frames. Data collection was carried out at 120K, using a frame time of 30 seconds and a detector distance of 60 mm. The optimized strategy used for data collection consisted of six phi and five omega scan sets, with 0.5° steps in phi or omega; completeness was 99.1%. A total of 3192 frames were collected. Final cell constants were obtained from the xyz centroids of 9886 reflections after integration.

From the systematic absences, the observed metric constants and intensity statistics, space group was chosen initially; subsequent solution and refinement confirmed the correctness of this choice. The asymmetric unit contains one molecule of the complex, two Cl$^-$ ions, and 7.38 (determined by refinement; see below) molecules of water (for the complex, Z=2; Z'=1). The structure was solved using SuperFlip (Palatinus et al., *J. Appl. Cryst.*, 40:786 (2007), which is hereby incorporated by reference in its entirety), and refined (full-matrix-least squares) using the Oxford University *Crystals for Windows* program (Betteridge et al., *J. Appl. Cryst.*, 36:1487 (2003); Prout et al., CAMERON, Chemical Crystallography Laboratory, Oxford, UK (1996), which are hereby incorporated by reference in their entirety). All ordered non-hydrogen atoms were refined using anisotropic displacement parameters. After location of H atoms on electron-density difference maps, the H atoms were initially refined with soft restraints on the bond lengths and angles to regularize their geometry (C—H in the range 0.93-0.98 Å and $U_{iso}$(H) in the range 1.2-1.5 times $U_{eq}$ of the parent atom), after which the positions were refined with riding constraints (Cooper et al., *J. Appl. Cryst.*, 43:1100-1107 (2010), which is hereby incorporated by reference in its entirety). Four of the six amide groups were found to be disordered. The disorder for each of the four pairs was modeled as a two-component disorder, and refined with each sum constrained to be 1.0. The components and their occupancies are: [N(12), C(50), C(51), C(52)/N(112), C(150), C(151), C(152); 0.438/0.562(6)]; [N(104), C(114), C(115), C(116)/O(12), N(4), C(14), C(15), C(16); 0.612/0.388(5)]; [C(124), c(125)/c(24), C(25); 0.529/0.471(15)]; and [N(10), C(41), C(42), C(43)/N(110), C(141), C(142), C(143); 0.408/0.592(11)]. All the modeled disordered components were refined using isotropic displacement parameters. Difference electron-density maps revealed a number of water solvate molecules. Five of the water molecules, O(7) through O(11), were ordered and H atoms could be located. Atom O(12) had a short "self-contact" of 2.22 Å and thus could not be present in amounts greater than 50%; however, since O(12) was hydrogen-bonded to N(4), we chose to constrain its occupancy to that of N(4), 0.388(5). Water molecules assigned as O(13) and O(14) were disordered, and the corresponding H atoms could not be located. Modeling of the disorder was not attempted. The final least-squares refinement converged to $R_1$=0.0499 (I>2σ(I), 13102 data) and $wR_2$=0.1283 (F$^2$, 15924 data, 738 parameters). The final CIF is available as supporting material. Two CheckCIF Alert A and three B items arise from the disorder model and the disorder in O atoms O(13) and O(14); accordingly, a validation response from item appears in the CIF.

Figure 3B:
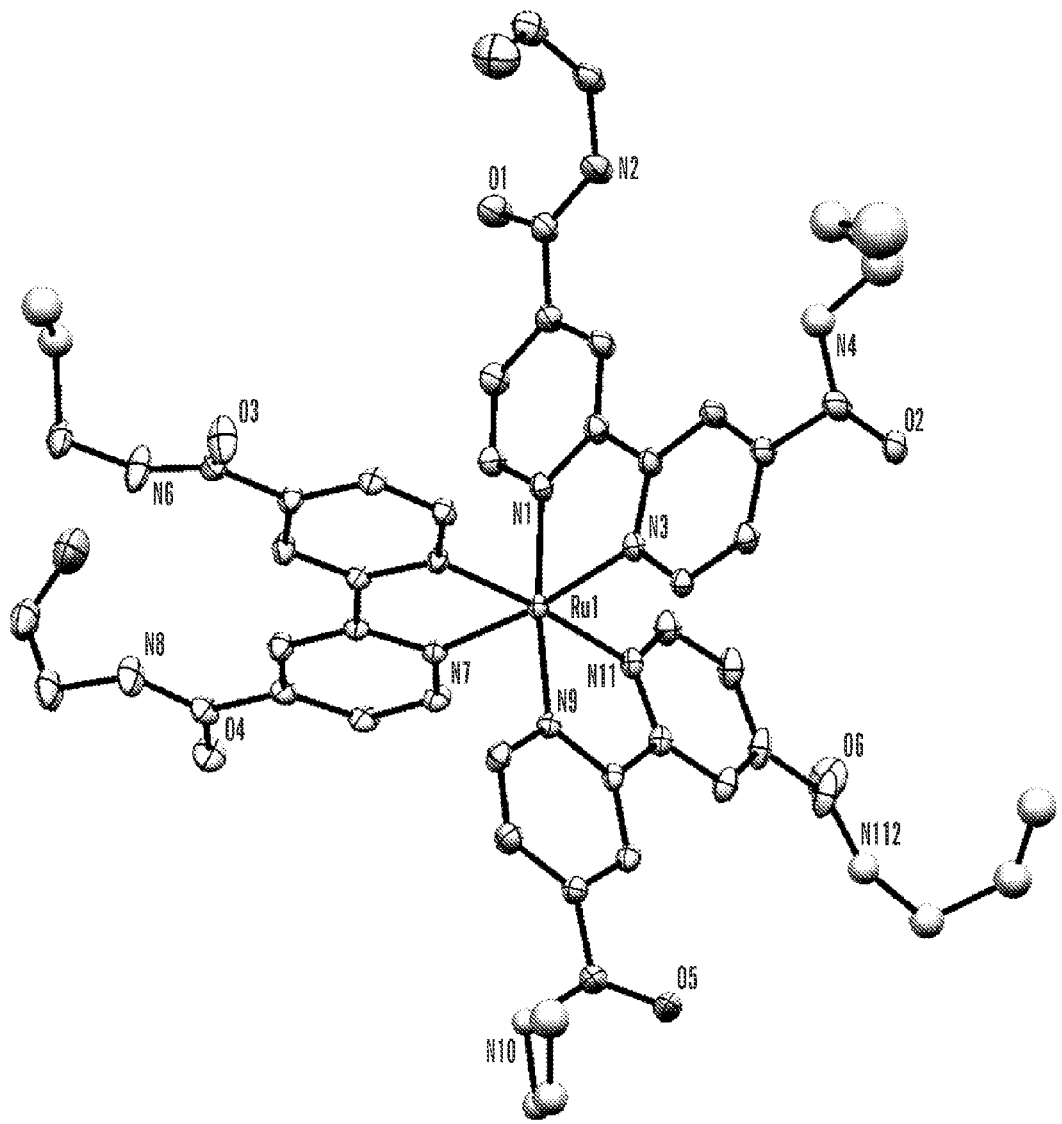
FIG. 3B shows the crystal structure of an active cross-linker in accordance with one embodiment of the present technology. Thermal ellipsoids set at 50% probability. For clarity, the Cl⁻ counter ions and all hydrogen atoms were omitted.

The crystal structure of the cross-linker (Formula I) is shown in FIG. 3B. The three bipyridine ligands around the Ru atom form a propeller-like trigonal arrangement. The coordination by the nitrogen atoms is close to octahedral. The results indicate that the active cross-linker of Formula I remains a similar geometry to the known crystal structure of $[Ru(bipy)_3]^{2+}$ (Low et al., *ActaCrystallographica Section B-Structural Science*, 68:137-149 (2012); Pointillart et al., *J. Am. Chem. Soc.*, 129:1327-1334 (2007), which are hereby incorporated by reference in their entirety). Among the six N-allylacetamide groups, two of them located on different bipyridine ligands are rigid, the other four have small flexibilities. The stereochemical configuration of the active cross-linker of Formula I makes itself an inherent 3D cross-linker.

Example 6—General Method of Preparation of Gel Disks

Figure 5:
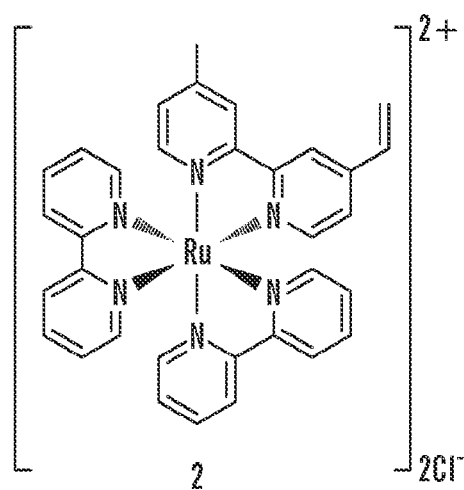
FIG. 5 shows the chemical structure of a Ru-catalyst 2.

After characterizing the physiochemical and structural properties of the active cross-linker of Formula I, a photo polymerization process was used to fabricate active gels. As described supra, the active cross-linker of Formula I and two distinct monomers, N-isopropylacrylamide (NIPAAm) and allylamine were used for a polymerization that results in active gels, $Gel_1$ and $Gel_2$, respectively. Both $Gel_1$ and $Gel_2$ employ the active cross-linker of Formula I as the cross-linkers to construct a 3D polymeric network. During the BZ reaction, the cross-linkers switch between reduced ($[RuL_3]^{2+}$, L=N,N'-diallyl-[2,2'-bipyridine]-4,4'-dicarboxamide) and oxidized state ($[RuL_3]^{3+}$). As the comparisons for $Gel_1$ and $Gel_2$, $Gel_3$ (Yoshida et al., *J. Am. Chem. Soc.*, 118:5134-5135 (1996), which is hereby incorporated by reference in its entirety) and $Gel_4$ use $[Ru(bipy)_2L']^{n+}$ (L'=4-methyl-4'-vinyl-2,2'-bipyridine, n=2 or 3) (FIG. 5) as pendants attached to the networks of poly(N-isopropylacrylamide) and poly(allylamine), respectively.

Based on reported procedures (Xia et al., *Angew. Chem.-Int. Edit.*, 37:551-575 (1998); Beebe et al., *Nature*, 404:588 et seq. (2000), which are hereby incorporated by reference in their entirety), rapid-prototyped photomasks (Qin, *Adv. Mater.*, 8:917 et seq. (1996), which is hereby incorporated by reference in its entirety) were used to define the diameters of the gel disks as 300-500 μm and a polycarbonate mold was used to restrict the heights of the gels as 100-200 μm. The photo-initiated polymerization was carried out in an ice-water bath during a relatively short reaction time (10-30 minutes).

For the production of $Gel_1$ and $Gel_2$ disks, the mixture for polymerization was prepared by dissolving monomer (N-isopropylacrylamide (NIPAAm) and allylamine, respectively), cross-linker of Formula I, and Irgacure 2959 (photoinitiator) in mixed solvent of methanol and DI water. After filling the mixture into a polycarbonate mold, a mask was applied on the top of the mold and the set-up was exposed under an Omicure light source for 10-30 minutes. To make comparison $Gel_3$ and $Gel_4$ disks, monomer (N-isopropylacrylamide and allylamine, respectively), ruthenium catalyst (FIG. 5), N,N'-methylenebisacrylamide (BIS) (cross-linker), and Irgacure 2959 were dissolved in mixed solvent of methanol and DI water and followed the same procedure of making $Gel_1$ and $Gel_2$. The Gel disks were immersed in DI water for dialysis for 3 days before further tests.

Example 7—Rheology

Rheology experiments were performed in an ARES-G2 rheometer with plain plate geometry (25 mm diameter).

Figure 6A:
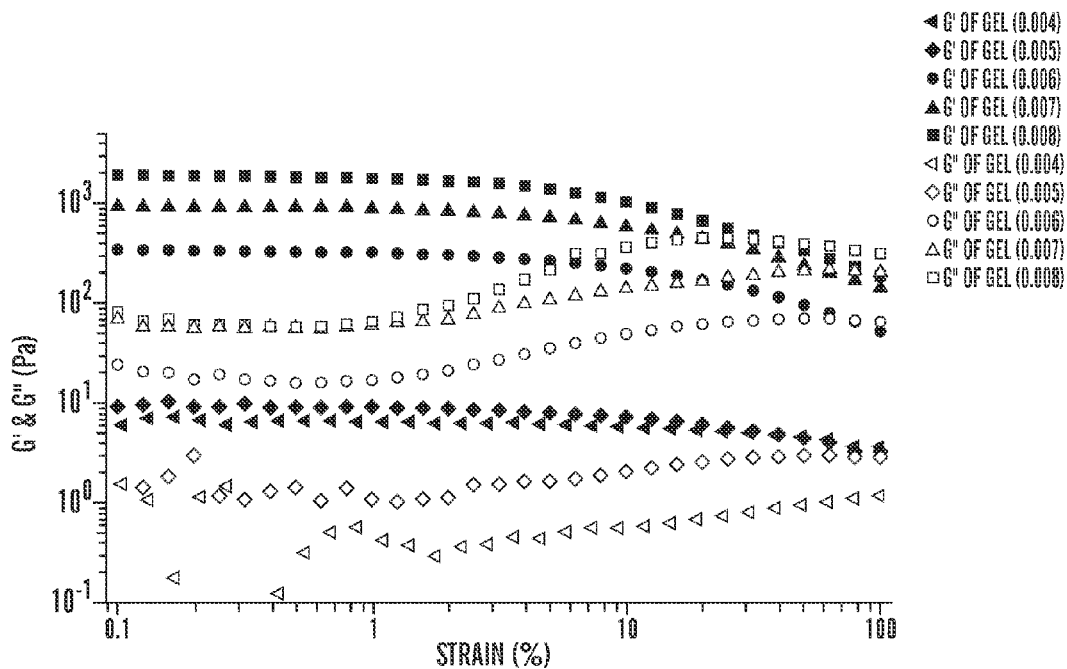
FIGS. 6A and B show strain dependence (FIG. 6A) and frequency dependence (FIG. 6B) of dynamic storage modulus (G') and loss modulus (G") of a gel series with different molar ratios of active cross-linker and monomer N-isopropylacrylamide (NIPAAm).
Figure 6B:
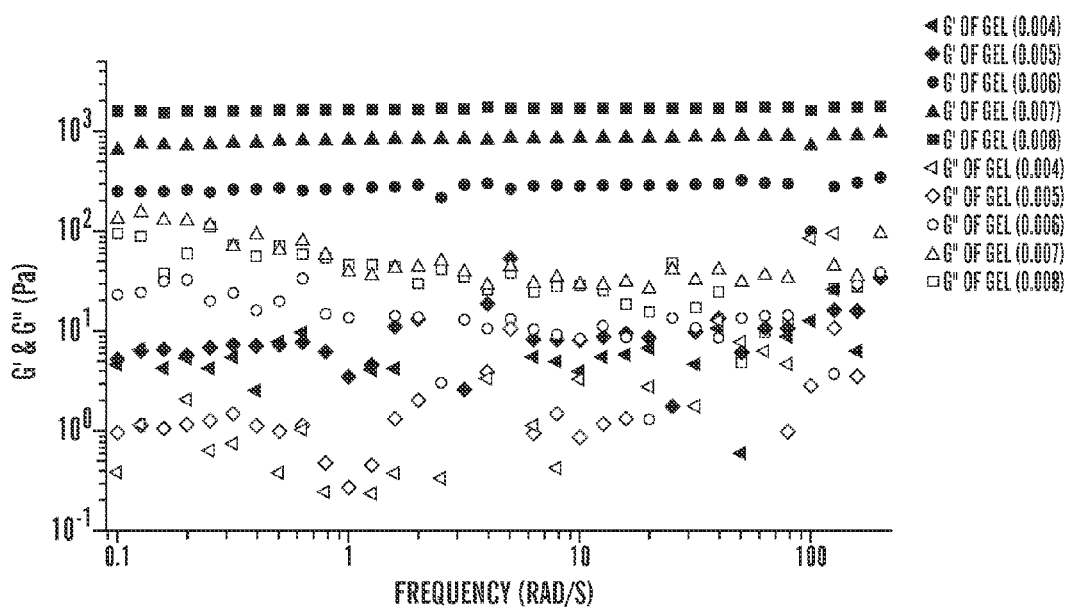
Figure 7:
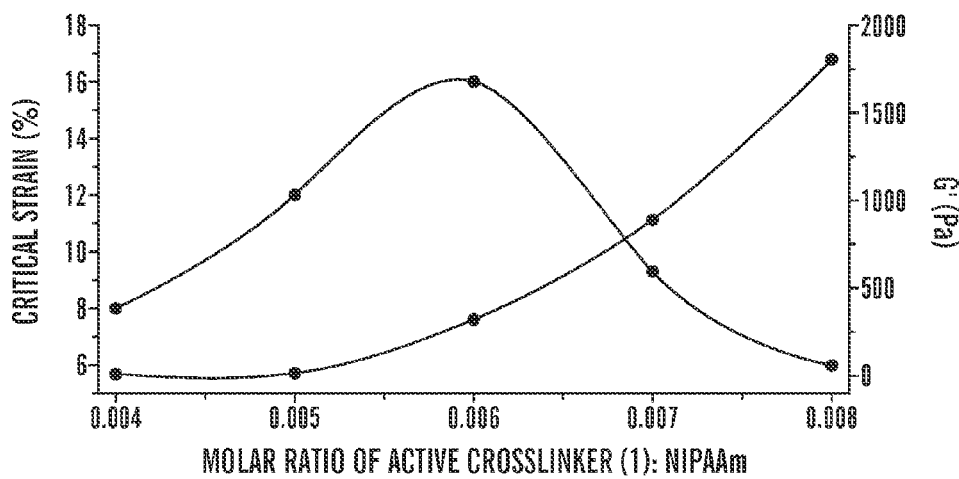
FIG. 7 shows the critical strain (upper line) and the storage moduli (lower line, at 0.5% strain) of gels in accordance with certain embodiments of the present technology versus the mole ratios of active cross-linker and monomer NIPAAm applied for polymerizations.

By controlling the initial ratio of the monomers versus the active cross-linker, gels with proper elasticity were obtained (FIGS. 6 and 7). For example, $Gel_1$ and $Gel_2$ polymerized by the active cross-linker of Formula I and the monomer at a ratio of 0.004:1 achieved the optimal cross-linking density and changed volume during the BZ reaction. When the molar ratio of active cross-linker versus NIPAAm was smaller than 0.004, no bulk gel was obtained. The molar ratios of the monomer, ruthenium catalyst (FIG. 5), and the cross-linker (BIS) were 1:0.015:0.012 for the synthesis of comparison $Gel_3$ and $Gel_4$.

FIGS. 6A and B show the strain dependence (FIG. 6A) and frequency dependence (FIG. 6B) of dynamic storage modulus (G') and loss modulus (G") of gel series with different molar ratios of active cross-linker of Formula I and monomer NIPAAm. Referring to FIG. 6, the storage moduli of all five gels were essentially independent of frequency, indicating a highly cross-linked three-dimensional structure within the gel (e.g., a continuous network formation). Regardless of the amount of cross-linker present, the value of storage modulus/loss modulus (G'/G") was always about 10, indicating a widely cross-linked structure.

FIG. 7 shows the critical strain (upper line) and the storage moduli (lower line, at 0.5% strain) of the gels versus the mole ratios of active cross-linker of Formula I and monomer NIPAAm applied for polymerizations. As shown in FIG. 7, the critical strain initially increased with the molar ratio and reached a maximum at the ratio of 0.006, after which it decreased. These results suggested that increasing the amount of cross-linker leads to increased brittleness of the gel beyond the optimal density. The storage modulus (G') at strain amplitude 0.5% was also measured, a value far below the critical strain of the gel, so that the polymer network remained intact. The G' increased almost exponentially with the amount of cross-linker.

Example 8—Fluorescent Images of Gels

Fluorescent images were recorded on a Marianas Spinning Disk Confocal Microscope which included a Zeiss Axlovert 200 M inverted microscope, Yokogawa CSU22 Spinning Disk, PhotoMetrics Cascade II, HBO 100 W Eplfluorescence Lamp, SlideBook 5, Leica M76 dissecting scope, and KL 1500 LCD light source.

Figure 8A:
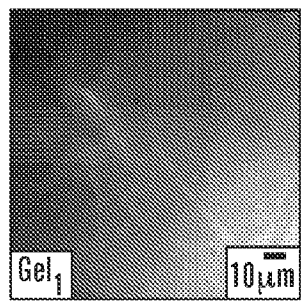
FIGS. 8A-D show confocal fluorescent images and 3D images of active polymeric gels in accordance with certain embodiments of the present technology (Gel$_1$ and Gel$_2$).
Figure 8B:
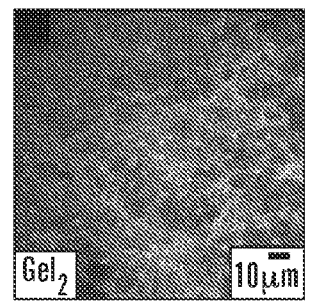
Figure 8C:
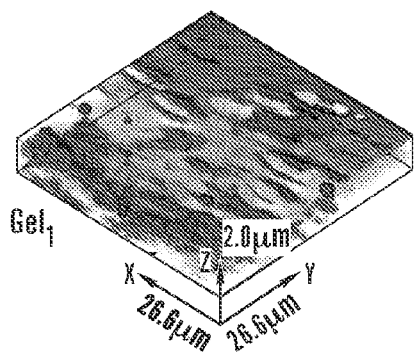
Figure 8D:
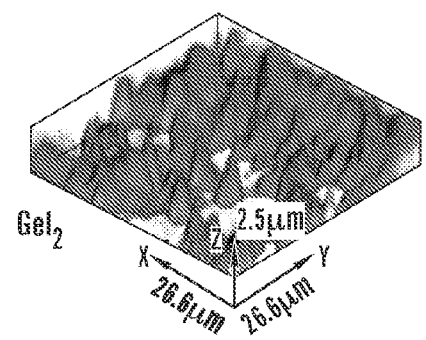
Figure 9A:
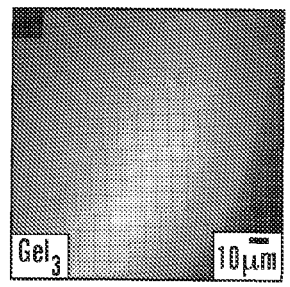
FIGS. 9A-D show confocal fluorescent images and 3D images of comparison polymeric gels (Gel$_3$ and Gel$_4$).
Figure 9B:
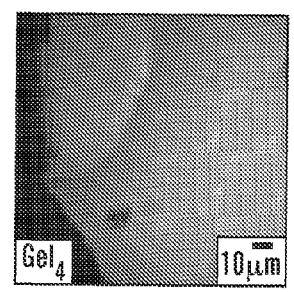
Figure 9C:
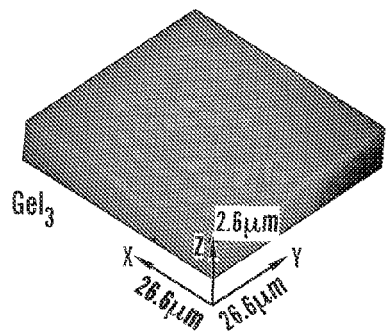
Figure 9D:
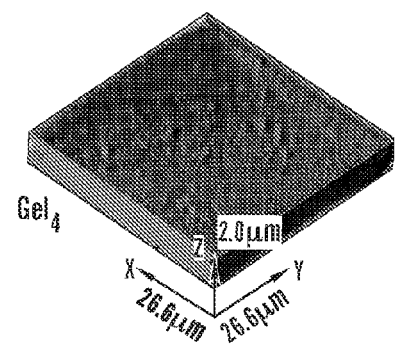

To understand the microstructure in the gels made by the active cross-linker of Formula I, confocal microscopy was used to image $Gel_1$ and $Gel_2$ at the reduced state since the active cross-linker of Formula I at the reduced state fluoresces strongly and stably upon the excitation at 488 nm. Fluorescent images (FIGS. 8A-D) indicated that $Gel_1$ and $Gel_2$ have different microstructures. For example, while $Gel_1$ showed largely homogeneous fluorescence (FIG. 8A) and some elliptical fluorescent dots (3.3×2.5 μm), $Gel_2$ showed a fluorescent porous network composed by interconnected micrometer size clots (FIG. 8B). In addition, the 3D rendered images (FIGS. 8C and 8D) obtained from a Z-scan series of fluorescent confocal images of $Gel_1$ and $Gel_2$ further confirmed that the cross-linkers distributed more homogenously in $Gel_1$ than in $Gel_2$ despite the inhomogeneity of the cross-linkers in both Gel$_1$ and Gel$_2$. As the comparison, the fluorescent images and the 3D rendered images of Gel$_3$ and Gel$_4$ (FIG. 9A-D) both showed quite homogeneous fluorescence, suggesting that the complexes ([Ru(bipy)$_2$L']$^{2+}$), as the pendants, distributed evenly in Gel$_3$ and Gel$_4$. In addition, Gel$_1$ (or Gel$_3$) and Gel$_2$ (or Gel$_4$) also exhibited different appearances. For example, Gel$_1$ or Gel$_3$ is more transparent than Gel$_2$ or Gel$_4$, a difference that likely originates from the different polymer backbones. These results indicated that while the difference in the monomers hardly influenced the distribution of the pendants in Gel$_3$ and Gel$_4$, the monomers in Gel$_1$ and Gel$_2$ likely also contributed to the heterogeneous distribution of the cross-linkers in Gel$_1$ and Gel$_2$.

Example 9—Chemomechanical Behaviors of Gels

Figure 10:
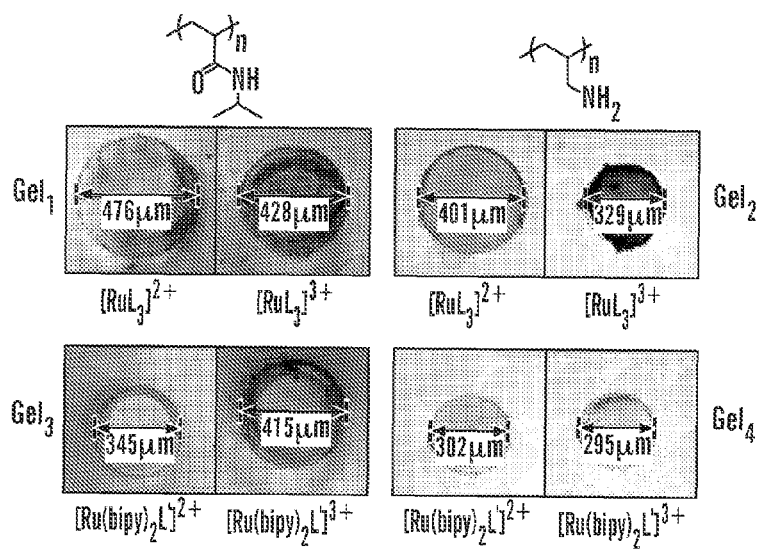
FIG. 10 shows optical images (top view) of active polymeric gels in accordance with certain embodiments of the present technology, Gel$_1$ and Gel$_2$, and comparison polymeric gels, Gel$_3$ and Gel$_4$ (the polymer chains are shown in the first row) at reduced state (by treating with Ce(NO$_3$)$_3$) and oxidized state (by treating with Ce(SO$_4$)$_2$ solution) at 24° C. The dotted circles indicate the edges of the gels.

The difference in the microstructures of the active gels, indeed, resulted in their different chemomechanical behaviors during redox reactions (FIG. 10). Upon the oxidization by cerium sulfate solution, both Gel$_1$ and Gel$_2$ shrank, but Gel$_2$ exhibited relatively bigger volume change than that of Gel$_1$. The shrink of Gel$_1$ and Gel$_2$ at the oxidized state also made them appear darker due to increased UV-Vis absorption. Unlike Gel$_1$ and Gel$_2$, upon oxidation, Gel$_3$ swelled, but Gel$_4$ hardly changed its volume. These results confirmed that the use of the active cross-linkers not only leads to a drastically different response to redox switch from those of the gels containing the [Ru(bipy)$_2$L']$^{n+}$ (n=2 or 3) as the pendants, but also allowed polymers other than poly(N-isopropylacrylamide) to form active gels that exhibited chemomechanical behaviors (i.e., redox reactions inducing volume changes).

Figure 11A:
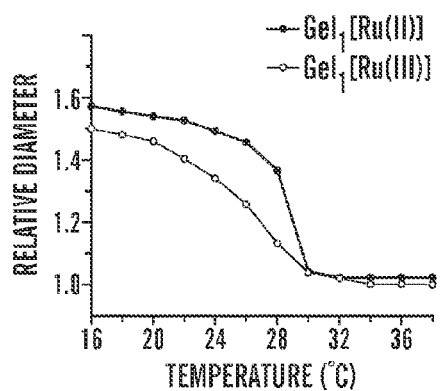
FIGS. 11A-F show volume changes of active polymeric gels in accordance with certain embodiments of the present technology (FIGS. 11A-B and 11E-F) and comparison gels (FIGS. 11C-D).
Figure 11B:
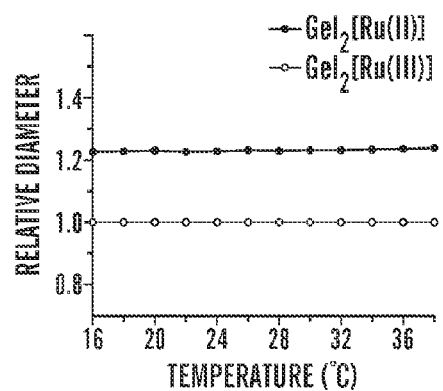
Figure 11C:
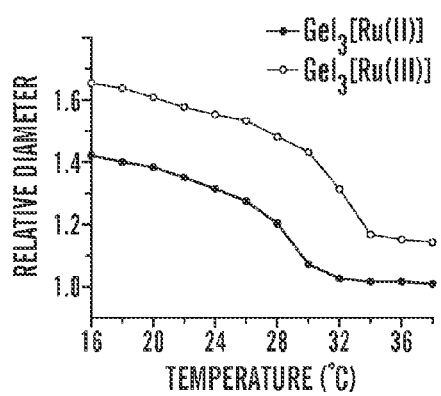
Figure 11D:
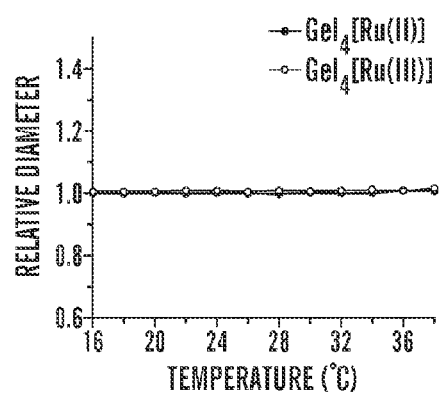

To further understand the correlation of the molecular structures and the behavior of the active gels, volume changes versus temperature at oxidized and reduced states of the gels (FIGS. 11A-D) were compared. Being defined by dividing the diameter of the gel at its minimum volume state, the relative diameters of all four gels changed in quite different manners. Gel$_1$, due to its thermo-responsive poly (NIPAAm) backbone (Schild, *Prog. Polym. Sci.*, 17:163-249 (1992), which is hereby incorporated by reference in its entirety), swelled upon decreasing the temperature at either oxidized or reduced states and exhibited temperature-dependent phase transitions at about 28° C. and 24° C. for the reduced and oxidized states, respectively (FIG. 11A). In the range of temperatures tested, Gel$_1$, in an oxidized state, shrank in different ratios relative to its reduced state, except at above 30° C., where little volume difference was exhibited between its two states (FIG. 11A). Unlike Gel$_1$, the volume of Gel$_2$, being independent to the change of temperature, shrank in a constant ratio compared to its reduced state (FIG. 11B). As a comparison with Gel$_1$, Gel$_3$ (Yoshida et al., *J. Am. Chem. Soc.*, 118:5134-5135 (1996), which is hereby incorporated by reference in its entirety), also containing poly(NIPAAm) backbones, swelled in an oxidized state compared to its reduced state over the entire temperature range tested (FIG. 11C). Similar to Gel$_1$, Gel$_3$ exhibited temperature-dependent phase transition at the reduced and oxidized state, similar to the results reported in literature (Yoshida et al., *J. Am. Chem. Soc.*, 118:5134-5135 (1996), which is hereby incorporated by reference in its entirety). Unlike Gel$_1$, Gel$_2$, and Gel$_3$, the volume of Gel$_4$ was essentially independent to the change of redox states or the temperature (FIG. 11D). In addition, although Gel$_1$ contained much fewer (1/5) Ru centers than Gel$_3$ did, the maximum difference of relative diameters in reduced and oxidized state of Gel$_1$ reached half of the difference of that of Gel$_3$, implying higher efficiency of chemomechanical conversion per redox center (Ru(II/III)) when it serves as the cross-linkers rather than as pendants. Clearly, the same was true for the cases of Gel$_2$ and Gel$_4$. These results further confirmed the unique merits of the active cross-linker.

Figure 11E:
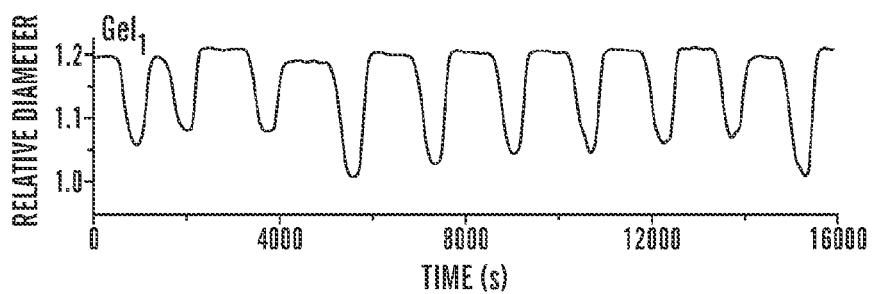
Figure 11F:
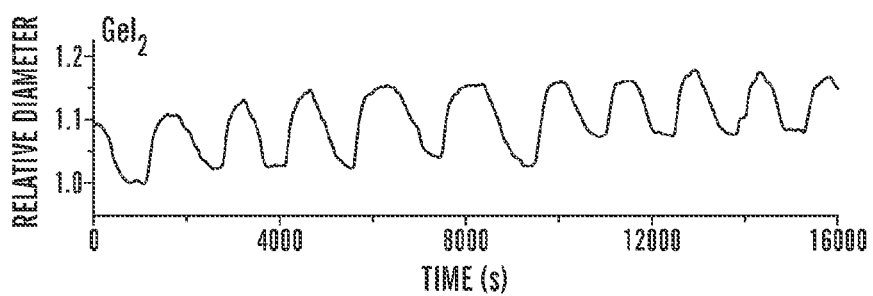

Because the BZ reaction offers a convenient experimental setting (Taylor et al., *Angew. Chem.-Int. Edit.*, 50:10161-10164 (2011); Ueki et al., *Angew. Chem.-Int. Edit.*, 51:11991-11994 (2012), which are hereby incorporated by reference in their entirety) to further confirm that the active cross-linkers confer active gels, the chemomechanical behaviors of Gel$_1$ and Gel$_2$ were evaluated during the BZ reaction. As shown in FIG. 11E, Gel$_1$ oscillated with an average period of 1650 seconds and a maximum relative diameter change of 18%. Similarly, Gel$_2$ oscillated with an average period of 1550 seconds and relative diameter change 12% (FIG. 11F). Thus, the autonomous chemomechanical oscillations of Gel$_1$ and Gel$_2$ during the BZ reaction demonstrate that the use of active cross-linkers is a powerful approach to develop active gels.

Example 10—SEM Images of Gel$_1$

SEM images were recorded on a NVision 40 Dual Beam Focused Ion Beam Imaging System.

Figure 12A:
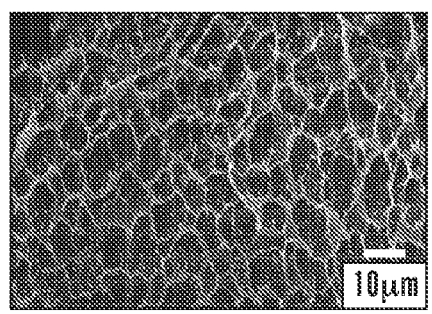
FIGS. 12A and B show SEM images of a freeze dried active polymeric gel in accordance with one embodiment of the present technology (Gel$_1$) at a reduced state (FIG. 12A) and an oxidized state (FIG. 12B).
Figure 12B:
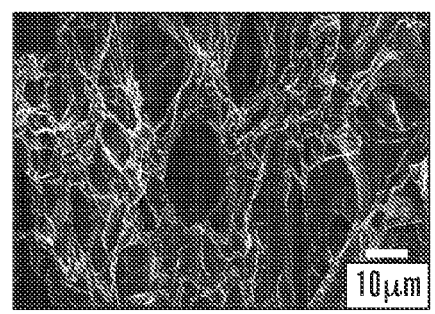

The shrink of Gel$_1$ at the oxidized state (FIG. 10) is an anti-intuitive result because it would expected that the increase of charges on the [RuL$_3$]$^{3+}$ complexes would result in repulsion and to cause the gel to swell. However, the scanning electron microscopy (SEM) of Gel$_1$ (FIGS. 12A-B) in reduced and oxidized states exhibits the transition of porous structure to condense structure upon oxidation of the [RuL$_3$]$^{2+}$ cross-linkers. This observation may fit an alternative interpretation: in the hyper cross-linked system, the octahedral geometry of the active cross-linker of Formula I leads to a genuine 3D network, in which the [RuL$_3$]$^{3+}$ cross-linker serves as the joint center of several polymer chains. Because the [RuL$_3$]$^{3+}$ are highly restricted within the cross-linked network, upon oxidation, the [RuL$_3$]$^{n+}$ cross-linkers attract extra counter ions into the network. The influx of counter ions, in fact, increase the electrostatic interactions between the ions, which likely expulses water molecules out of the network and eventually induces the collapse of the polymer network. Although other factors may contribute the volume shrink, the results form confocal imaging and SEM confirm that the active cross-linker plays a critical role for the chemomechanical volume change of the active gels.

As described supra, the [Ru(bipy)$_3$]$^{n+}$ based active cross-linker of Formula I and two distinct monomers, N-isopropylacrylamide (NIPAAm) and allylamine were used for a polymerization that results in active gels, Gel$_1$ and Gel$_2$, respectively. During the BZ reaction, the cross-linkers switch between reduced ([RuL$_3$]$^{2+}$, L=N,N'-diallyl-[2,2'-bipyridine]-4,4'-dicarboxamide) and oxidized state ([RuL$_3$]$^{3+}$), which caused Gel$_1$ and Gel$_2$ to shrink at the oxidized state and to swell at the reduced state. As the comparisons for Gel$_1$ and Gel$_2$, Gel$_3$ and Gel$_4$ used [Ru (bipy)$_2$L']$^{n+}$ (U=4-methyl-4'-vinyl-2,2'-bipyridine, n=2 or 3) (FIG. 5) as pendants attached to the networks of poly(N-isopropylacrylamide) and poly(allylamine), respectively. Under the same condition of the BZ reaction used for Gel₁ and Gel₂, Gel₃ swelled and Gel₄ exhibited little change of volume when the pendants were in oxidized state ([Ru(bipy)₂L']³⁺). Such drastic contrasts of volume changes confirmed that the molecular architecture determines the chemomechanical behavior of the active gels. Moreover, the transformation of a thermally insensitive polymer (i.e., poly(allylamine)) into a self-oscillatory material by the active cross-linkers of the present technology illustrates that polymerization with active cross-linkers is an effective approach to generate active gels.

Having thus described the basic concept of the invention, it will be rather apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and scope of the invention. Additionally, the recited order of processing elements or sequences, or the use of numbers, letters, or other designations therefore, is not intended to limit the claimed processes to any order except as may be specified in the claims. Accordingly, the invention is limited only by the following claims and equivalents thereto.

What is claimed:

1. A polymeric material comprising:
   a plurality of polymer subunits; and
   an active cross-linker selected from the group consisting of:

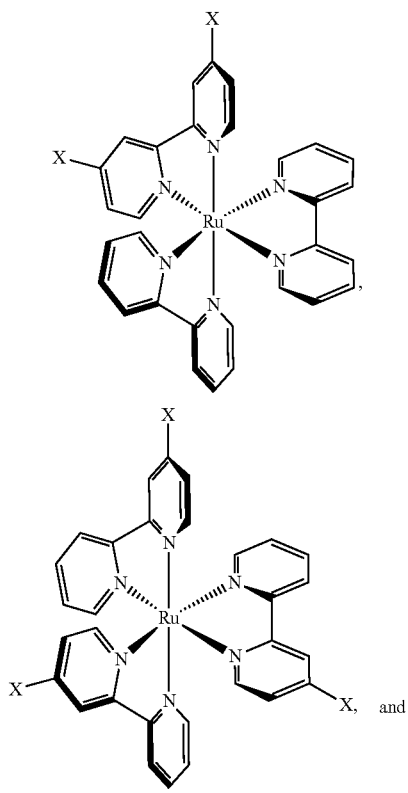

where X is and n is an integer from 1 to 20; and where R is and n is an integer from 1 to 20;
wherein the active cross-linker is covalently linked to the plurality of polymer subunits by two to six covalent bonds.

2. The polymeric material according to claim 1, wherein the polymeric material is selected from the group consisting of a gel, an elastomer, a rubber, a film, a foam, an aerogel, and a sponge.

3. The polymeric material according to claim 1, wherein the polymer subunits are selected from the group consisting of monomers, oligomers, and combinations thereof.

4. The polymeric material according to claim 1, wherein the active cross-linker is selected from the group consisting of 5. The polymeric material according to claim 1, wherein the active cross-linker is selected from the group consisting of wherein R is and n is an integer from 1 to 20.

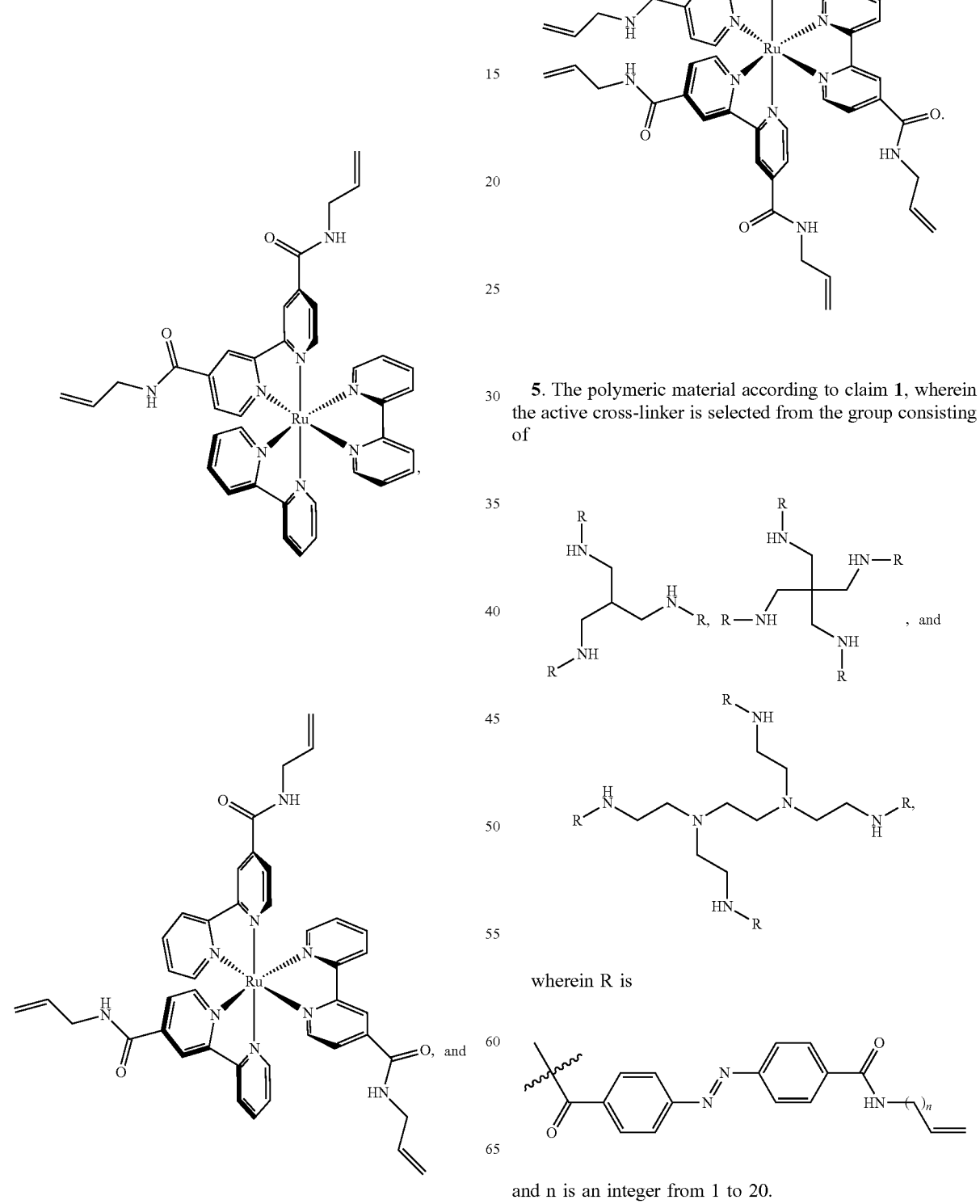

6. The polymeric material according to claim 1, wherein the molar ratio of the polymer subunit to the active cross-linker is from about 1:1 to about $1\times10^8$:1.

7. The polymeric material according to claim 6, wherein the molar ratio of the polymer subunit to the active cross-linker is about 1:0.004.

8. A chemomechanical material comprising a polymeric material according to claim 1,
wherein the active cross-linker is covalently linked to the plurality of polymer subunits to form a stimuli responsive shape changing polymeric network.

9. The chemomechanical material according to claim 8 selected from the group consisting of a biomedical product, a cosmetic product, and an actuator.

10. A compound having the formula:

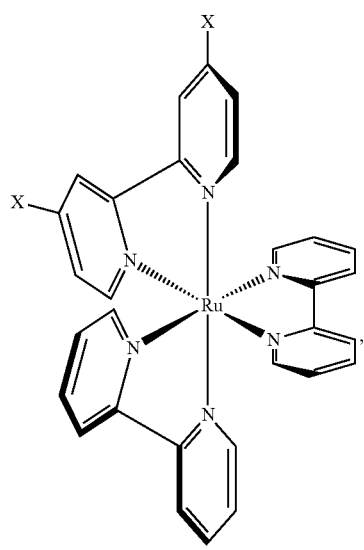

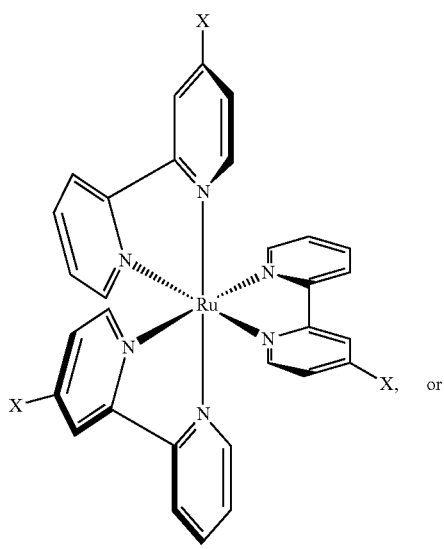

-continued

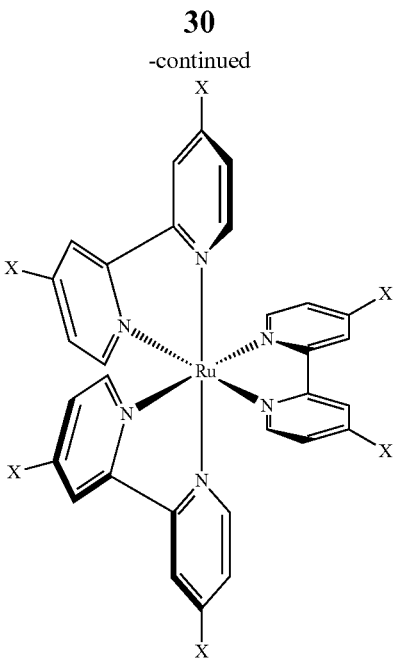

where each X has the formula

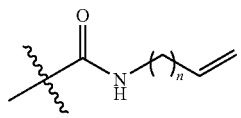

wherein n is an integer from 1 to 20.

11. The compound according to claim 10, wherein the compound is selected from the group consisting of:

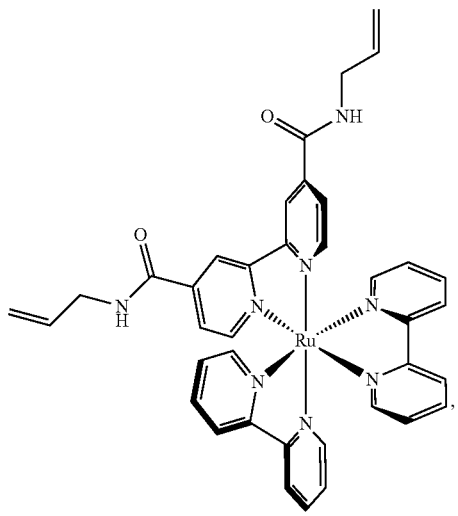

-continued
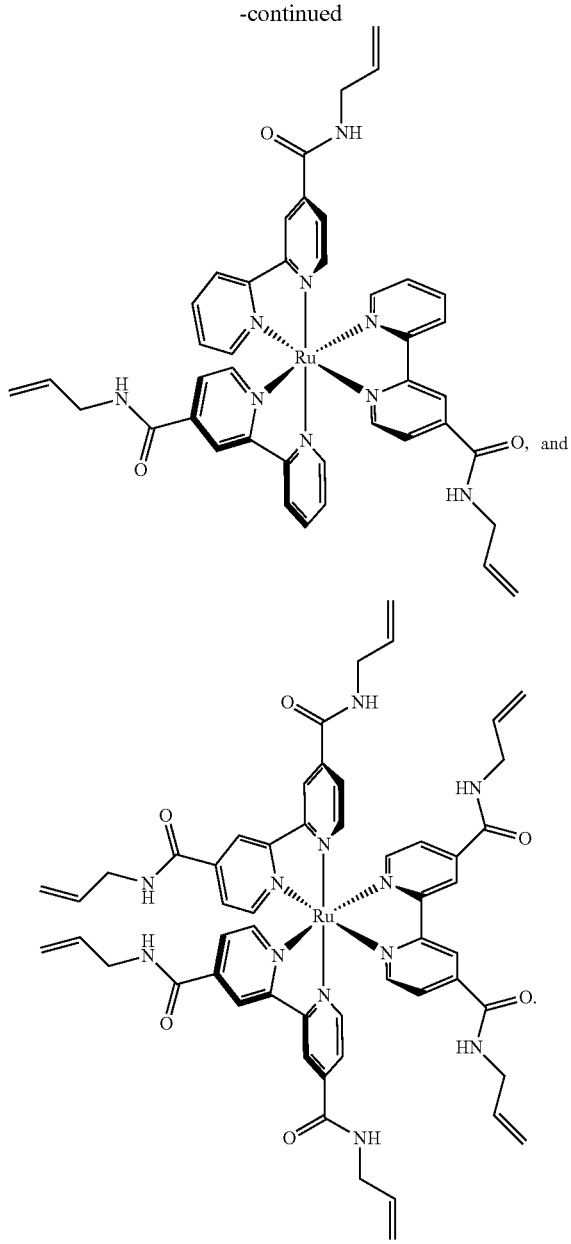
12. A compound of the formulae:
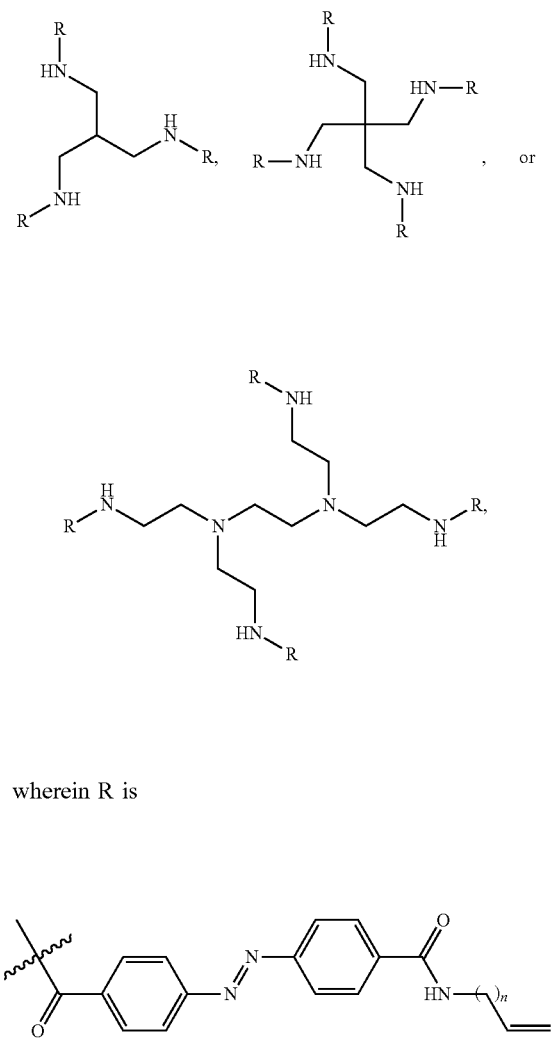
wherein R is
and n is an integer from 1 to about 20.
* * * * *